US012770713B2

(12) United States Patent
Loukas et al.

(10) Patent No.: US 12,770,713 B2
(45) Date of Patent: Oct. 20, 2026

(54) GENERATIVE PROTEIN DESIGN WITH COMPOSABLE ENERGY-BASED MODELS

(71) Applicants: Genentech, Inc., South San Francisco, CA (US); Hoffmann-La Roche, Inc., Little Falls, NJ (US)

(72) Inventors: Andreas Loukas, Basel (CH); Stephen Robert Ra, New York, NY (US); Andrew Martin Watkins, San Francisco, CA (US); Richard A. Bonneau, New York, NY (US); Kyunghyun Cho, New York, NY (US); Nathan Christopher Frey, New York, NY (US); Vladimir Gligorijevic, New Brunswick, NJ (US); Simon Paul Kelow, Washington, DC (US)

( * ) Notice: Subject to any disclaimer, the term of this patent is extended or adjusted under 35 U.S.C. 154(b) by 0 days.

(21) Appl. No.: 19/273,028

(22) Filed: Jul. 17, 2025

(65) Prior Publication Data

US 2025/0342904 A1 Nov. 6, 2025

Related U.S. Application Data

(63) Continuation of application No. PCT/US2024/011804, filed on Jan. 17, 2024.

(60) Provisional application No. 63/480,287, filed on Jan. 17, 2023.

(51) Int. Cl.
*G16B 15/20* (2019.01)
*G16B 30/10* (2019.01)
*G16B 40/20* (2019.01)

(52) U.S. Cl.
CPC ............. *G16B 15/20* (2019.02); *G16B 30/10* (2019.02); *G16B 40/20* (2019.02)

(58) Field of Classification Search
None
See application file for complete search history.

(56) References Cited

U.S. PATENT DOCUMENTS

2004/0162413 A1 8/2004 Watkins et al.

OTHER PUBLICATIONS

Narayanan, Arjun, Benjamin D. Sellers, and Matthew P. Jacobson. “Energy-based analysis and prediction of the orientation between light-and heavy-chain antibody variable domains.” Journal of molecular biology 388.5 (2009): 941-953.*

Gligorijević, Vladimir, et al. “Function-guided protein design by deep manifold sampling.” bioRxiv (2021): 2021-12.*

International Searching Authority, International Search Report and Written Opinion, mailed May 15, 2024, for International Patent Application No. PCT/US2024/011804 (12 pages).

Du et al., 2020, “Energy-based models for atomic-resolution protein conformations,” arxiv.org, Cornell University Library, XP081653951.

Strokach et al., 2022, “Deep generative modeling for protein design,” Current Opinion in Structural Biology, 72:226-236, XP093027599.

Tagasovska et al., 2022, “A Pareto-optimal compositional energy-based model for sampling and optimization of protein sequences,” arxiv.org, Cornell University Library, XP091348763.

* cited by examiner

*Primary Examiner* — G. Steven Vanni
(74) *Attorney, Agent, or Firm* — Jones Day

(57) ABSTRACT

A method may include identifying an input sequence. The input sequence or, in some cases, a fixed-length representation of the input sequence may be modified by applying a protein design computation model trained to approximate a distribution of protein sequences exhibiting certain desirable properties. The protein design computation model may include at least one energy-based model and a corresponding energy function. The at least one energy-based model may be applied to modify the input sequence while the corresponding energy function may be applied to determine the likelihood of the modified input sequence within the distribution of protein sequences exhibiting the desirable properties. An output sequence may be generated based on the modified input sequence upon determining that the likelihood of the modified input sequence within the distribution of protein sequences exhibiting the desirable properties satisfies one or more thresholds.

31 Claims, 10 Drawing Sheets

700

GENERATIVE PROTEIN DESIGN WITH COMPOSABLE ENERGY-BASED MODELS

CROSS REFERENCE TO RELATED APPLICATION

This application is a bypass continuation of International Patent Application No. PCT/US2024/011804, entitled "GENERATIVE PROTEIN DESIGN WITH COMPOSABLE ENERGY-BASED MODELS" and filed on Jan. 17, 2024, which claims priority to U.S. Provisional Application No. 63/480,287, entitled "GENERATIVE MODELS IN ANTIBODY DESIGN AND ENGINEERING: INTERPLAY BETWEEN MACHINE LEARNING AND PHYSICS-BASED DESIGN MODELS" and filed on Jan. 17, 2023, the disclosure of each of which are incorporated herein by reference in their entirety.

TECHNICAL FIELD

The subject matter described herein relates generally to protein design and more specifically to energy-based models (EBM) for generating protein sequences.

INTRODUCTION

Proteins are genetically encoded macromolecules whose diversity in size and chemical composition enable a gamut of functionalities. By regulating biological systems, proteins facilitate many essential cellular functions including, for example, enzymatic reactions, transport of molecules, regulation and execution of a number of biological pathways, cell growth, proliferation, nutrient uptake, morphology, motility, intercellular communication, and/or the like. A protein molecule may include one or more polypeptide chains, each of which including a sequence of amino acid residues linked together by peptide bonds (e.g., covalent peptide bonds). Of the 20 possible amino acid residues, each amino acid residue has the same backbone atoms (e.g., an amino group ($NH_2$), an α-carbon, and a carboxylic acid group (COOH)) coupled with different sidechain atoms (or R groups).

The primary structure of the protein molecule refers to the sequence of amino acid residues in each of the polypeptide chains in the protein molecule. The backbone atoms in adjacent amino acid residues that participate in the peptide bonds (e.g., covalent peptide bonds) therebetween give rise to a repeating sequence of atoms known as the polypeptide backbone (or backbone). The local folded structures (e.g., α helices, β pleated sheet, and/or the like) that form within an individual polypeptide chain due to interactions between the backbone atoms (e.g., amino hydrogen atoms, carboxyl oxygen atoms, and/or the like) are referred to as the secondary structure of the protein molecule. Further interactions (e.g., non-covalent bonds such as hydrogen bonding, ionic bonding, dipole-dipole interactions, and van der Waals forces) between the sidechains (or R-groups) of the amino acid residues in the protein molecule form the tertiary structure of the protein molecule. In protein molecules having multiple polypeptide chains, the protein molecule may also exhibit a quaternary structure, which is formed when the polypeptide chains are packed and held together by hydrogen bonds and van der Waals forces (e.g., between nonpolar sidechains).

The primary structure of the protein molecule may determine many critical properties of the protein molecule. For example, the primary structure of the protein molecule may determine the conformation or the three-dimensional structure (e.g., the tertiary structure) assumed by the protein molecule through the folding the constituent polypeptide chains. The three-dimensional structure of the protein molecule may contribute to its viability as a therapeutic. Accordingly, one notable objective of computational protein design is to construct one or more sequences of amino acid residues to exhibit a variety of desirable properties.

SUMMARY

Systems, methods, and articles of manufacture, including computer program products, are provided for an energy-based model (EBM) for protein sequence design. In some example embodiments, there is provided a system that includes at least one processor and at least one memory. The at least one memory may include program code that provides operations when executed by the at least one processor. The operations may include: identifying an input sequence; modifying the input sequence by at least applying a protein design computation model trained to approximate a first distribution of protein sequences exhibiting the first property, the protein design computation model including a first energy-based model (EBM) and or a first energy function, and the protein design computation model modifying of the input sequence by at least applying the first energy-based model (EBM) to modify the input sequence, and applying the first energy function to determine a first likelihood of the modified input sequence within the first distribution of protein sequences exhibiting the first property; and generating, based at least on the modified input sequence, an output sequence upon determining that the first likelihood of the modified input sequence within the first distribution of protein sequences exhibiting the first property satisfies one or more thresholds.

In another aspect, there is provided a method for an energy-based model (EBM) for proteins sequence design. The method may include: identifying an input sequence; modifying the input sequence by at least applying a protein design computation model trained to approximate a first distribution of protein sequences exhibiting the first property, the protein design computation model including a first energy-based model (EBM) and or a first energy function, and the protein design computation model modifying of the input sequence by at least applying the first energy-based model (EBM) to modify the input sequence, and applying the first energy function to determine a first likelihood of the modified input sequence within the first distribution of protein sequences exhibiting the first property; and generating, based at least on the modified input sequence, an output sequence upon determining that the first likelihood of the modified input sequence within the first distribution of protein sequences exhibiting the first property satisfies one or more thresholds.

In another aspect, there is provided a computer program product including a non-transitory computer readable medium storing instructions. The instructions may cause operations may executed by at least one data processor. The operations may include: identifying an input sequence; modifying the input sequence by at least applying a protein design computation model trained to approximate a first distribution of protein sequences exhibiting the first property, the protein design computation model including a first energy-based model (EBM) and or a first energy function, and the protein design computation model modifying of the input sequence by at least applying the first energy-based model (EBM) to modify the input sequence, and applying the first energy function to determine a first likelihood of the modified input sequence within the first distribution of protein sequences exhibiting the first property; and generating, based at least on the modified input sequence, an output sequence upon determining that the first likelihood of the modified input sequence within the first distribution of protein sequences exhibiting the first property satisfies one or more thresholds.

In some variations of the methods, systems, and non-transitory computer readable media, one or more of the following features can optionally be included in any feasible combination.

In some variations, the first energy function may be parameterized by a plurality of parameters comprising the first energy-based model (EBM).

In some variations, the input sequence may be modified based at least on an output of the first energy function such that each modification increases the first likelihood of the modified input sequence generated therefrom being within the first distribution of protein sequences exhibiting the first property.

In some variations, the generating of the output sequence includes: applying, to the input sequence, a first modification to generate a first modified input sequence; applying, to the input sequence, a second modification to generate a second modified input sequence; applying the first energy function to determine, for each of the first modified input sequence and the second modified input sequence, a respective likelihood of the first modified input sequence and the second modified input sequence being within the first distribution of protein sequences exhibiting the first property; and further modifying, based at least on the respective likelihood of each of the first modified input sequence and the second modified input sequence being within the first distribution, one of the first input modified sequence and the second input modified sequence.

In some variations, the first distribution of protein sequences exhibiting the first property may be a probability distribution that includes, for each position within a fixed-length sequence, a probability of each possible amino acid residue occupying that position.

In some variations, the protein design computation model may be further trained to approximate a second distribution of protein sequences exhibiting a second property.

In some variations, the training of the protein design computation model may include adjusting a plurality of parameters of a second energy-based model (EBM) such that a second energy function parameterized by the plurality of parameters outputs an energy value corresponding to a second likelihood of a sequence within the second distribution of protein sequences.

In some variations, the input sequence may be modified by at least applying a composition of the first energy-based model (EBM) and the second energy-based model (EBM) representative of a third distribution of protein sequences exhibiting the first property and the second property.

In some variations, the input sequence may be modified based at least on a combination of the first energy function and the second energy function.

In some variations, the modifying of the input sequence may further include: applying the second energy-based model (EBM) to further modify the input sequence; applying the second energy function to determine a second likelihood of the further modified input sequence within the second distribution of protein sequences exhibiting the second property; and generating, based at least on the further modified input sequence, the output sequence upon determining that a sum the first likelihood of the further modified input sequence within the first distribution of protein sequences and the second likelihood of the further modified input sequence within the second distribution of protein sequences satisfies one or more thresholds.

In some variations, the sum may correspond to a third likelihood of the modified input sequence within a third distribution of protein sequences exhibiting the first property and the second property.

In some variations, the input sequence may be modified based on the sum of the first likelihood and the second likelihood such that each modification increases the third likelihood of the modified input sequence within the third distribution of protein sequences exhibiting the first property and the second property.

In some variations, the modifying of the input sequence may further include: generating a first modified input sequence having a first modification to the input sequence; determining, based at least on a combination of the first energy function and the second energy function, a first energy value indicative of a third likelihood of the first modified input sequence within a third distribution of protein sequences exhibiting the first property and the second property; generating a second modified input sequence having a second modification to the input sequence; determining, based at least on the combination of the first energy function and the second energy function, a second energy value indicative of the third likelihood of the second modified input sequence within the third distribution of protein sequences exhibiting the first property and the second property; and further modifying, based at least on a comparison of the first energy value and the second energy value, one of the first modified input sequence and the second modified input sequence.

In some variations, the first modified input sequence may be further modified instead of the second modified input sequence based at least on the first energy value of the first modified input sequence being lower than the second energy value of the second modified input sequence.

In some variations, the first property and the second property may be a different one of expression, binding affinity towards another molecule, non-specificity, stability, immunogenicity, human-ness, and self-association.

In some variations, the protein design computation model may be further trained to approximate a third distribution of protein sequences exhibiting a third property.

In some variations, the training of the protein design computation model may include adjusting a plurality of parameters of a third energy-based model (EBM) such that a third energy function parameterized by the plurality of parameters outputs an energy value corresponding to a third likelihood of a sequence within the third distribution of protein sequences.

In some variations, the input sequence may be modified by at least applying a composition of the first energy-based model (EBM), the second energy-based model (EBM), and the third energy-based model (EBM). The output sequence may be generated based on the modified input sequence upon determining that a sum of a respective likelihood of the modified input sequence within the first distribution of protein sequences, the second distribution of protein sequences, and the third distribution of protein sequences satisfies the one or more thresholds.

In some variations, a fixed-length representation of the input sequence may be generated. The first energy-based model (EBM) may be applied to modify the fixed-length representation of the input sequence.

In some variations, the fixed-length representation of the input sequence may include a gap character at each position in the input sequence without an amino acid residue having a structural role associated with the position.

In some variations, the modifying of the input sequence may include changing an identity of an amino acid residue at one or more positions within the fixed-length representation of the input sequence.

In some variations, the modifying of the input sequence may include at least one of deleting an amino acid residue occupying a position within the fixed-length representation of the input sequence by at least replacing the amino acid residue with a gap character, and inserting an amino acid residue at a position within the fixed-length representation of the input sequence by at least replacing a gap residue occupying the position with the amino acid residue.

In some variations, a plurality of sample sequences exhibiting the first property may be identified. The protein design computation model may be trained by at least adjusting one or more parameters of the first energy-based model to increase a similarity between one or more sequences output by the first energy-based model (EBM) and the plurality of sample sequences.

In some variations, the plurality of sample sequences may be a subset of known protein sequences that excludes one or more known protein sequences failing to exhibit the first property.

In some variations, the training of the protein design computation model may include adjusting the one or more parameters of the first energy-based model (EBM) to increase the first likelihood of a sequence generated by the first energy-based model within the first distribution of protein sequences exhibiting the first property.

In some variations, the training of the protein design computation model may include adjusting the one or more of parameters of the first energy-based model (EBM) such that the first energy function parameterized by the one or more parameters outputs a lower energy value for a first sequence that is within the first distribution of protein sequences than for a second sequence that is outside of the first distribution of protein sequences.

In some variations, the first energy-based model may be an artificial neural network (ANN).

In some variations, an adjustable segment and a fixed segment may be determined within the input sequence. The first energy-based model (EBM) may be applied to modify the adjustable segment but not the fixed segment of the input sequence.

In some variations, the adjustable segment may include a crystallizable fragment (Fc) of an antibody having the input sequence.

In some variations, the fixed segment may include an antigen binding fragment (Fab), a variable fragment (Fv), a complementarity determining region (CDR), and/or a Vernier zone of an antibody having the input sequence.

In another aspect, there is provided a system that includes at least one processor and at least one memory. The at least one memory may include program code that provides operations when executed by the at least one processor. The operations may include: identifying a first plurality of sample sequences exhibiting a first property; training, based at least on the first plurality of sample sequences, a protein design computation model to approximate a first distribution of protein sequences exhibiting the first property, the training of the protein design computation model includes adjusting a first plurality of parameters of a first energy-based model (EBM) to increase a first similarity between one or more first sequences output by the first energy-based model (EBM) and the first plurality of sample sequences exhibiting the first property, and determining a first energy function parameterized by the first plurality of parameters to output a first energy value corresponding to a first likelihood of the one or more first sequences within the first distribution of protein sequences exhibiting the first property; and generating an output sequence exhibiting the first property by at least applying the first energy-based model (EBM) of the trained protein design computation model to modify, based at least on the first energy function, an input sequence.

In another aspect, there is provided a method for an energy-based model (EBM) for proteins sequence design. The method may include: identifying a first plurality of sample sequences exhibiting a first property; training, based at least on the first plurality of sample sequences, a protein design computation model to approximate a first distribution of protein sequences exhibiting the first property, the training of the protein design computation model includes adjusting a first plurality of parameters of a first energy-based model (EBM) to increase a first similarity between one or more first sequences output by the first energy-based model (EBM) and the first plurality of sample sequences exhibiting the first property, and determining a first energy function parameterized by the first plurality of parameters to output a first energy value corresponding to a first likelihood of the one or more first sequences within the first distribution of protein sequences exhibiting the first property; and generating an output sequence exhibiting the first property by at least applying the first energy-based model (EBM) of the trained protein design computation model to modify, based at least on the first energy function, an input sequence.

In another aspect, there is provided a computer program product including a non-transitory computer readable medium storing instructions. The instructions may cause operations may executed by at least one data processor. The operations may include: identifying a first plurality of sample sequences exhibiting a first property; training, based at least on the first plurality of sample sequences, a protein design computation model to approximate a first distribution of protein sequences exhibiting the first property, the training of the protein design computation model includes adjusting a first plurality of parameters of a first energy-based model (EBM) to increase a first similarity between one or more first sequences output by the first energy-based model (EBM) and the first plurality of sample sequences exhibiting the first property, and determining a first energy function parameterized by the first plurality of parameters to output a first energy value corresponding to a first likelihood of the one or more first sequences within the first distribution of protein sequences exhibiting the first property; and generating an output sequence exhibiting the first property by at least applying the first energy-based model (EBM) of the trained protein design computation model to modify, based at least on the first energy function, an input sequence.

In some variations of the methods, systems, and non-transitory computer readable media, one or more of the following features can optionally be included in any feasible combination.

In some variations, a second plurality of sample sequences exhibiting a second property may be identified. The protein design computation model may be further trained, based at least on the second plurality of sample sequences, to approximate a second distribution of protein sequences exhibiting the second property. The further training of the protein design computation model may include adjusting a second plurality of parameters of a second energy-based model (EBM) to increase a second similarity between one or more second sequences output by the second energy-based model (EBM) and the second plurality of sample sequences exhibiting the second property, and determining a second energy function parameterized by the second plurality of parameters to output a second energy value corresponding to a second likelihood of the one or more second sequences within the second distribution of protein sequences exhibiting the second property.

In some variations, the generating of the output sequence may include: applying the first energy-based model (EBM) and the second energy-based model (EBM) to modify the input sequence; applying the first energy function to determine, for the modified input sequence, the first energy value indicative of the first likelihood of the modified input sequence within the first distribution of protein sequences exhibiting the first property; applying the second energy function to determine, for the modified input sequence, the second energy value indicative of the second likelihood of the modified input sequence within the second distribution of protein sequences exhibiting the second property; and generating, based at least on the modified input sequence, an output sequence upon determining that a sum of the first energy value and the second energy value satisfies one or more thresholds.

In some variations, the first property and the second property may be a different one of expression, binding affinity towards another molecule, non-specificity, stability, immunogenicity, human-ness, and self-association.

In some variations, the first plurality of sample sequences may be a subset of known protein sequences that excludes one or more known protein sequences failing to exhibit the first property.

In some variations, the training of the protein design computation model may include: applying the first energy-based model (EBM) having a first adjustment to generate a first plurality of modified sequences; applying the first energy-based model (EBM) having a second adjustment to generate a second plurality of modified sequences; determining that the first plurality of modified sequences is more similar to the first plurality of sample sequences than the second plurality of modified sequences; and in response to determining that the first plurality of modified sequences is more similar to the first plurality of sample sequences than the second plurality of modified sequences, further training the protein design computation model by applying a third adjustment to the first energy-based model (EBM).

In some variations, each of the first adjustment and the second adjustment may include a change to one or more weights and/or biases of the first energy-based model (EBM).

In some variations, the first energy-based model may modify the input sequence based on an output of the first energy function such that each modification increases the first likelihood of the modified input sequence generated therefrom being within the first distribution of protein sequences exhibiting the first property.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which can include a non-transitory computer-readable or machine-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including, for example, to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to energy-based models (EBMs) for the design of protein sequences, it should be readily understood that such features are not intended to be limiting. The claims that follow this disclosure are intended to define the scope of the protected subject matter.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Figure 1:
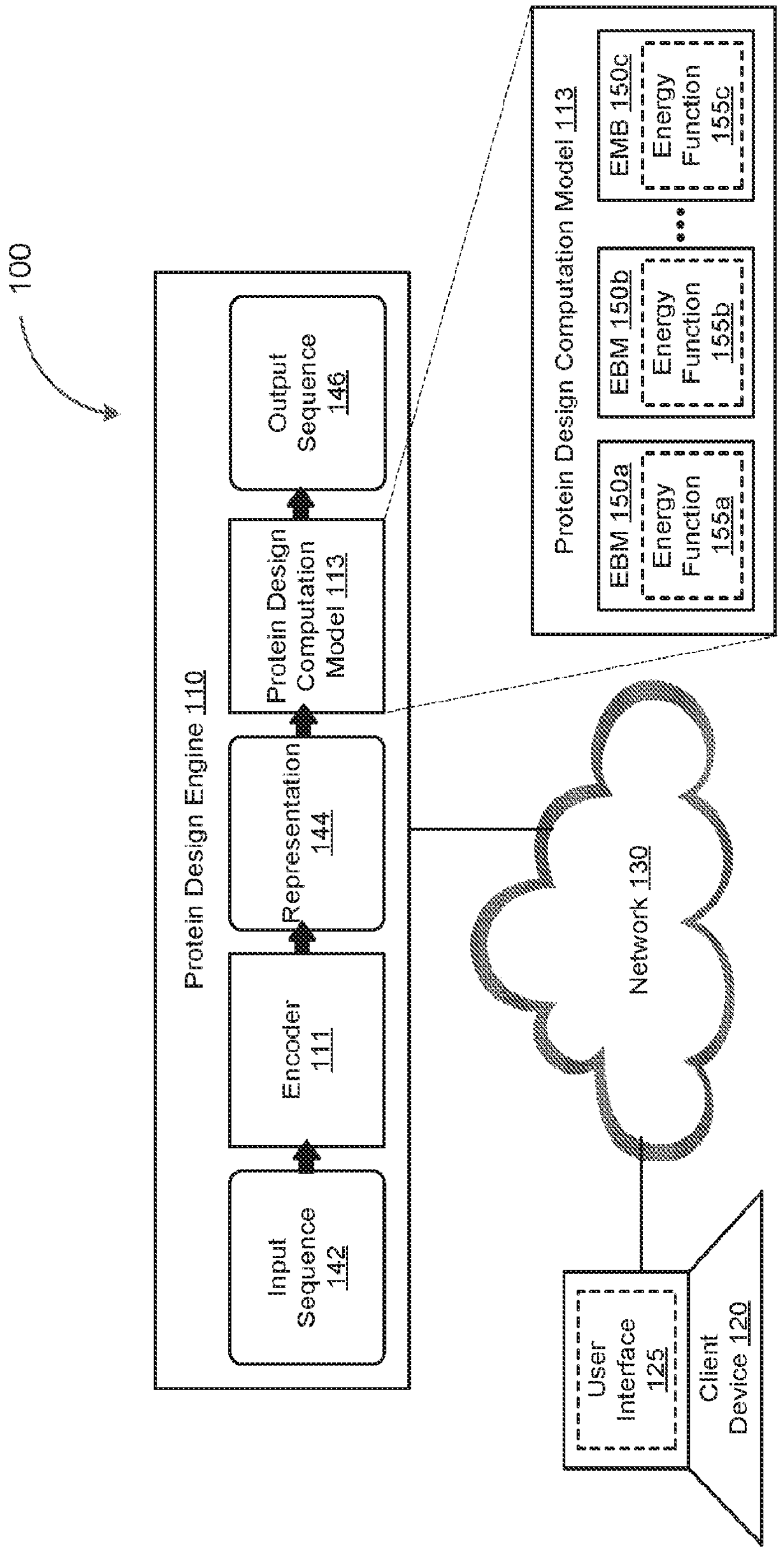
FIG. 1 depicts a system diagram illustrating an example of a protein design system, in accordance with some example embodiments.

Computational protein design aims to generate protein sequences that exhibit a variety of desirable properties. In the context of large molecule drug discovery, the properties of a protein sequence may determine its viability as a protein-based therapeutic. For example, in some cases, a protein sequence may be computationally designed for increased affinity and targetability, enhanced in vivo stability and pharmacokinetics, improved cell permeability, and reduced immunogenicity. However, computational protein design is a challenging and resource intensive task at least because the combinatorial search space of every possible permutation of amino acid residues that can form a protein sequence is vast (e.g., 201 dimensions for a protein sequence of length L) but sparsely populated by protein sequences with therapeutic value. In fact, the vast majority of protein sequences in the combinatorial search space will not exhibit any function at all. Thus, even if protein sequences are screened entirely in silico, a brute force search of the combinatorial space is too computationally expensive to be a feasible solution. Instead, in some example embodiments, a protein design computation model may generate output protein sequences by learning a probability distribution of known protein sequences (or a subset of known protein sequences) and sampling therefrom.

In some example embodiments, the protein design computation model may include at least one energy-based model (EBM) trained to approximate, based at least on a training set of sample sequences, a corresponding distribution (e.g., probability distribution). In some cases, the at least one energy-based model (EBM) may learn the distribution (e.g., the probability distribution) of the sample sequences in the training set by at least capturing, probabilistically, the regularities, rules, organizations, and constraints present in the sample sequences. In the present context, the distribution (e.g., probability distribution) of the sample sequences in the training set may correspond to the likelihood of different possible permutations of amino acid residues forming the sample sequences in the training set. It should be appreciated that the likelihood of a particular permutation of amino acid residues does not correspond to the frequency with which the exact same permutation of amino acid residues occurs within the training set. Instead, in some cases, the likelihood of a particular permutation of amino acid residues may correspond to the joint probability of certain amino acid residues occupying different positions in a protein sequence given what is observed across the sample sequences in the training set which, as noted, may be a specific subset of protein sequence such as a specific class or family of protein sequences, protein sequences exhibiting specific properties, and/or the like. However, the computation of the distribution (e.g., probability distribution) of the sample sequences may be intractable because the aforementioned joint distribution is a high dimensional joint distribution in the context of protein sequences (e.g., an n-dimensional joint probability distribution for n-length protein sequences). Accordingly, as described in more details below, the protein design computation model may approximate the distribution of the sample sequences through sampling techniques such as Markov Chain Monte Carlo (MCMC) sampling.

In some example embodiments, the training of the energy-based model (EBM) may include determining a corresponding energy function that outputs the likelihood of a given permutation of amino acid residues within the distribution of the sample sequences in the training set. Once the energy-based model is trained, the corresponding energy function may also approximate the distribution (e.g., probability distribution) of the sample sequences in the training set by at least generating an output corresponding to the likelihood of a protein sequence within the distribution of the sample sequences in the training set. For example, in some cases, the energy function may assign, to a protein sequence, a value (e.g., an energy value) indicative of whether the permutation of amino acid residues forming the protein sequence is in or out of the distribution of the sample sequences in the training set. Accordingly, once trained, the energy-based model may be applied to successively modify, based at least on the output of the energy function, an input sequence to generate protein sequences with an incrementally higher likelihood of being within the distribution of the sample sequences in the training set.

In some example embodiments, the energy function of the energy-based model (EBM) may be parametrized by a machine learning model. For example, in cases where the energy-based model is implemented with an artificial neural network (e.g., a convolutional neural network and/or the like), the parameters of the energy-based model may correspond to the weights and/or biases applied by the neurons in each successive layer of the artificial neural network. In some cases, the energy function may be determined by at least adjusting the parameters of the energy-based model such that the value (e.g., energy value) determined by the energy function for a protein sequence corresponds to the likelihood of the protein sequence within the distribution of the sample sequences in the training set. In particular, the parameters of the energy function may be adjusted to increase (or maximize) the likelihood of sequences that are similar to the sample sequences in the training set. In some cases, this may mean reducing (or minimizing) the energy of those protein sequences that are similar to the sample sequences in the training set. For instance, the parameters of the energy-based model (EBM) may be adjusted in order for the energy function to output a lower value (e.g., a lower energy value) for a first protein sequence that is similar to the sample sequences in the training set than for a second protein sequence that is less similar to the training sequences in the training set. In doing so, the resulting energy function may approximate the distribution (e.g., probability distribution) of the sample sequences in the training set. In particular, the gradient of the energy function may correspond to changes in the density of sequences across the distribution (e.g., probability distribution) such that the values (e.g., energy values) output by the energy function may guide subsequent sequence generation towards sampling higher density regions of the distribution populated by sequences that are more similar to the sample sequences.

In some example embodiments, due to the intractable nature of the distribution (e.g., probability distribution) of the sample sequences in the training set (e.g., an n-dimensional joint probability distribution for n-length protein sequences), the distribution may be approximated through a sampling technique, such as Markov Chain Monte Carlo (MCMC) sampling and/or the like. For example, in some cases, the training of the energy-based model may include a gradient based Markov Chain Monte Carlo (MCMC) sampling (e.g., Langevin Markov Chain Monte Carlo sampling and/or the like) to approximate the gradient of the energy function. Each iteration of gradient based Markov Chain Mote Carlo (MCMC) sampling may include drawing one or more samples from the distribution of the sample sequences in the training set. In this context, a single sample may be said to be drawn from the distribution of the sample sequences in the training set by applying the energy-based model (EBM) to modify an input sequence. It should be appreciated that samples may be initially drawn from low density regions of the distribution, which are populated by sequences dissimilar to the sample sequences in the training set. Accordingly, in some cases, the parameters of the energy-based model (EBM) may be adjusted over successive iterations to increase the similarity between the sequences generated by the energy-based model and the sample sequences in the training set, thus shifting the sampling towards higher density regions of the distribution. Doing so may be tantamount to learning the probability distribution of the sample sequences in the training set such that the corresponding energy function outputs, for each sequence of amino acid residues, a value (e.g., energy value) indicative of the likelihood of the sequence being in the distribution of sample sequences in the training set. Thus, once the energy-based model (EBM) is trained, the energy function may output a lower energy for sequences sampled from high density regions of the distribution than for sequences sampled from low density regions of the distribution. Moreover, as described in more details below, in some cases, the gradient of the energy function, which refers to changes in the value (e.g., energy value) output by the energy function, may guide the generation of sequences towards sampling from the higher density regions of the distribution.

In some example embodiments, the distribution (e.g., probability distribution) of the sample sequences in the training set may be approximated through gradient based Markov Chain Monte Carlo (MCMC) sampling including, for example, Markov Chain Monte Carlo with Langevin dynamics (or Langevin Markov Chain Monte Carlo) and/or the like. In some cases, each iteration of gradient-based Markov Chain Monte Carlo sampling may include adjusting the parameters (e.g., weights, biases, and/or the like) of the energy-based model to increase the similarity between the sample sequences in the training set and the output sequences generated by the energy-based model modifying an input sequence. The adjustments made to the parameters of the energy-based model may be cumulative over successive iterations, with each subsequent iteration further adjusting a previously adjusted set of parameters that yielded output sequences with a greater similarity (e.g., lower Kullback-Leibler divergence) to the sample sequences in the training set. For example, in some cases, the energy-based model having a first set of adjusted parameters may be further adjusted during a subsequent iteration if the energy-based model having the first set of adjusted parameters yielded output sequences that are more similar to the sample sequences in the training set than the energy-based model having a second set of adjusted parameters.

In some example embodiments, once the energy-based model (EBM) is trained based on the sample sequences in the training set to approximate the distribution (e.g., probability distribution) of the sample sequences in the training set, the energy-based model may be applied to generate output sequences to have the same property as the sample sequences. For example, in some cases, the trained energy-based model may generate an output sequence by sampling the distribution of the sample sequences. Moreover, in some cases, the output sequence may be generated through Markov Chain Monte Carlo (MCMC) sampling, which may be guided by the energy function of the trained energy-based model to sample from incrementally higher density regions the distribution populated by the sample sequences in the training set. In cases where the output sequence is generated through gradient based Markov Chain Monte Carlo sampling (e.g., Langevin Markov Chain Monte Carlo (MCMC) and/or the like), each successive iteration may include sampling from a higher density region than a previous iteration by further modifying a modified sequence from that iteration assigned a value (e.g., energy value) by the energy function that indicates a greater similarity to the sample sequences in the training set than other previously modified sequences. For instance, in some cases, the trained energy-based model (EBM) may be applied to generate a first modified sequence and a second modified sequence. During a subsequent iteration, the trained energy-based model may be applied to further modify the first modified sequence instead of the second modified sequence if the first modified sequence is assigned a lower value (e.g., lower energy value) by the energy function than the second modified sequence.

In some example embodiments, the energy-based model (EBM) may generate an output sequence by applying, to an input sequence, one or more modifications that includes, for example, inserting an amino acid residue into the input sequence, deleting an amino acid residue from the input sequence, changing the identity of an amino acid residue in the input sequence, and/or the like. The inserting and deleting of one or more amino acid residues may result in a change in the length of the input sequence. In some cases, the length of the input sequence may change frequently throughout the generative process as one or more amino acid residues may be inserted and/or deleted during each iteration. As such, in some cases, the computational complexities that arise from the length of the input sequence changing during the generative process may be reduced by the energy-based model operating on a fixed-length representation of the input sequence instead of a conventional variable length representation of the input sequence. For example, in some cases, the input sequence may be rendered in a fixed length representation by applying a structural role-based numbering scheme in which each amino acid residue in the input sequence is assigned an integer position in the fixed length sequence (e.g., selected from a range of integers such as [1, 149]) based on the residue's structural role). A gap at any position in the fixed-length sequence where the input sequence lacks an amino acid residue having the corresponding structural role may be represented by a gap character. Accordingly, in some cases, each position in the fixed-length representation of the input sequence may be occupied either by one of the twenty possible amino acid residues (e.g., canonical amino acid residues) or a gap character. The insertion of an amino acid residue at an empty position in the input sequence may be accomplished by the energy-based model (EBM) replacing the gap character occupying the position with the amino acid residue. Meanwhile, the deletion of an amino acid residue occupying a position in the input sequence may be accomplished by the energy-based model replacing the amino acid residue at the position with a gap character.

In some example embodiments, the energy-based model (EBM) may be trained based on sample sequences exhibiting certain properties such that the output protein sequences generated by the energy-based model also exhibit the same properties. Accordingly, in some cases, instead of being trained to approximate the distribution (e.g., probability distribution) of all known protein sequences, the energy-based model (EBM) may be trained to approximate the distribution (e.g., probability distribution) of a subset of known protein sequences. For example, the sample sequences in the training set may be limited to a subset of known protein sequences from one or more specific classes or families of proteins (e.g., antibodies and/or the like). Alternatively and/or additionally, the sample sequences in the training set may be limited to a subset of known protein sequences that exhibit certain properties including, for example, expression, binding affinity towards another molecule (e.g., a viral antigen, a tumor antigen, and/or the like), non-specificity, stability, immunogenicity, human-ness, self-association, and/or the like. As described in more detail below, by limiting training to a subset of known protein sequences, the energy-based model (EBM) may be implemented with fewer parameters than the large language models (LLMs) typically used for computational protein sequence design (e.g., tens of thousands of parameters instead of millions or billions of parameters). As such, various embodiments of the energy-based model described herein may achieve state-of-the-art generative performance (or better than state-of-the-art generative performance) faster and with less computational resources and training data than traditional large language models.

In some example embodiments, the protein design computation model may include multiple energy-based models, each of which being trained to approximate the distribution (e.g., probability distribution) of protein sequences exhibiting a different property, such that output protein sequences are generated by a composition of the energy-based models to satisfy multiple properties. For example, in some cases, the protein design computation model may include a first energy-based model (EBM) trained to approximate a first distribution of protein sequences exhibiting a first property and a second energy-based model trained to approximate a second distribution of protein sequences exhibiting a second property. In some cases, the composition of the first energy-based model and the second energy-based model may be representative of a third distribution of protein sequences exhibiting the first property as well as the second property. Accordingly, an output sequence exhibiting both the first property and the second property may be generated by sampling from the third distribution of protein sequences. Moreover, in some cases, the protein design computation model may generate an output sequence by successively modifying an input protein sequence based on a combination of a first energy function of the first energy-based model and a second energy function of the second energy-based model. For instance, in some cases, the output sequence may be generated by successively modifying, based at least on a sum of a first output of the first energy function and a second output of the second energy function, the input sequence such that each successive modification to the input sequence increases the likelihood that the output sequence resulting therefrom is within the third distribution of protein sequences exhibiting the first property and the second property. In some cases, in addition to the first energy-based model and the second energy-based mode, the protein design computation model may further include a third energy-based model (EBM) trained to approximate a third distribution of protein sequences exhibiting a third property such that the output sequences of the protein design computation model exhibit the first property, the second property, and the third property.

In some example embodiments, the protein design computation model may modify an input sequence such that one or more output sequences generated therefrom exhibit better therapeutic properties such as increased affinity and targetability, enhanced in vivo stability and pharmacokinetics, improved cell permeability, and reduced immunogenicity. In some cases, the input sequence may be a known protein sequence, such as a non-human animal antibody identified through an immunization campaign. Alternatively, the input sequence may be a noise sequence, which may be a randomly ordered sequence of amino acid residues without known properties. In some cases, a first portion of the input sequence may be associated with one or more desirable properties (e.g., affinity) while a second portion of the input sequence may be associated with one or more undesirable properties (e.g., immunogenicity). As such, the modifications to the input sequence may be limited to the second portion of the input sequence while the first portion of the input sequence are preserved (or unchanged) throughout the generative process. For example, in cases where the input sequence is a non-human animal antibody with binding affinity towards a target epitope, the protein design computation model may modify the input sequence in order to humanize the input sequence and generate one or more output sequence with reduced immunogenicity. Accordingly, in some cases, the protein design computation model may generate one or more output sequences by modifying the framework region of the input sequence but not the complementarity determining regions (CDRs) of the input sequence. Doing so may increase the viability of the output sequences as protein-based therapeutics by at least reducing (or eliminating) the immunogenicity of the input sequence while preserving its binding affinity toward the target epitope. Furthermore, in some cases, the generation of output sequences that exhibit specific properties may increase and/or diversify the repertoire of known protein sequences with these properties.

FIG. 1 depicts a system diagram illustrating an example of a protein design system 100, in accordance with some example embodiments. Referring to FIG. 1, the protein design system 100 may include a protein design engine 110 and a client device 120 communicatively coupled via a network 130. The client device 120 may be a processor-based device including, for example, a workstation, a desktop computer, a laptop computer, a smartphone, a tablet computer, a wearable apparatus, and/or the like. The network 130 may be a wired network and/or a wireless network including, for example, a local area network (LAN), a virtual local area network (VLAN), a wide area network (WAN), a public land mobile network (PLMN), the Internet, and/or the like.

In some example embodiments, the protein design engine 110 may include an encoder 111 and a protein design computation model 113. In some cases, the protein design computation model 113 may modify an input sequence 142, for example, by modifying a representation 144 of the input sequence 142, in order to generate an output sequence 146. As shown in FIG. 1, the encoder 113 may generate, for ingestion by the protein design computation model 113, the representation 144 of the input sequence 142. The protein design computation model 113 may then generate, based at least on the representation 144 of the input sequence 142, the output sequence 146. For instance, in some cases, the protein design computation model 113 may generate the output sequence 146 by at least modifying, over multiple successive iterations, the representation 144 of the input sequence 142. In some cases, the input sequence 142 may be a noise sequence (e.g., a randomly ordered sequence of amino acid residues) without any known properties or a known protein sequence (e.g., a human or non-human antibody identified through an immunization campaign). The output sequence 146 that is generated during a single iteration by modifying the representation of the input sequence 142 may be considered a sample drawn from one or more distributions (e.g., probability distributions) of protein sequences approximated by the protein design computation model 113.

As described in more details below, in some cases, the protein design computation model 113 may modify the input sequence 142 by applying one or more energy-based models (EBMs), each of which being trained to approximate the distribution (e.g., probability distribution) of a specific set of sample sequences (e.g., a particular class (or family) of protein sequences, protein sequences exhibiting certain properties, and/or the like). Accordingly, in some cases, each successive modification of the input sequence 142 performed by the one or more energy-based models may increase (or maximize) the likelihood of the corresponding output sequence 146 being within the distribution (e.g., probability distribution) of the sample sequences used to train each energy-based model. That is, in some cases, each successive modification of the input sequence 142 may be akin to sampling from an increasingly higher density region of the distribution (e.g., probability distribution) of the sample sequences in the training set. In cases where the input sequence 142 is a noise sequence without any known properties, the output sequence 146 generated in the manner described herein may exhibit the same properties as the sample sequences. Where the input sequence 142 is a protein sequence having one or more known properties, the output sequence 146 may be generated to include modifications that improve upon the known properties of the input sequence 142. For example, in some cases, the modifications may increase a desirable property and/or reduce an undesirable property known to be present in the input sequence 142. Alternatively and/or additionally, the input sequence 142 may be modified such that the output sequence 146 exhibits one or more additional properties absent from the input sequence 142.

As noted, in some cases, instead of operating on the input sequence 142 directly, the protein design computation model 113 may modify the representation 144 of the input sequence 142. In some cases, the representation 144 may be a fixed-length representation of the input sequence 142, meaning that the representation 144 of the input sequence 142 may have a same length (e.g., a same quantity of positions or tokens) regardless of the quantity of amino acid residues forming the input sequence 142. The encoder 113 may generate the representation 144 to be a fixed-length representation of the input sequence 142 in a variety of different ways. For example, in some cases, the encoder 113 may apply a structural role based numbering scheme in order to generate the representation 144 of the input sequence 142. In instances where the input sequence 142 corresponds to an immunoglobulin protein (or an antibody), these structural roles may correspond to the amino acid residue occupying a particular complementarity determining region (CDR) loop or a framework region between a pair of complementarity determining region (CDR) loops. At any position of the representation 144 where the input sequence 142 lacks an amino acid residue having the structural role associated with that position, the representation 144 of the input sequence may include a gap character to indicate the corresponding void in the input sequence 142. As described in more details below, the insertion and deletion of amino acid residues from the input sequence 142, which changes the length of the input sequence 142, may be achieved with greater computational efficiency in instances where the representation 144 is a fixed-length representation of the input sequence 142 with gap characters to indicate the absence of an amino acid residues at certain positions in the input sequence 142.

In some example embodiments, the protein design computation model 113 may generate the output sequence 146 by applying one or more modifications to input sequence 142 or, in some cases, the representation 144 thereof. The one or more modifications may include changing an identity of one or more of the amino acid residues in the input sequence 142. For example, in some cases, the one or more modifications may include replacing, with a different amino acid residue, one or more of the amino acid residues in the representation 144 of the input sequence 142. Alternatively and/or additionally, the one or more modifications may include inserting and/or deleting one or more amino acid residues in the input sequence 142. As noted, the insertion and deletion of amino acid residues from the input sequence 142, which changes the length of the input sequence 142, may be realized with greater computational efficiency where the representation 144 is a fixed-length representation of the input sequence 142 with gap characters to indicate the absence of an amino acid residue at certain positions in the input sequence 142. For instance, in some cases, an amino acid residue may be inserted into the input sequence 142 by replacing, with a character corresponding to the amino acid residue, a gap character in the representation 144 of the input sequence 142. Meanwhile, the deletion of an amino acid residue from the input sequence 142 may be achieved by replacing, with a gap character, the character corresponding to the amino acid residue in the representation 144 of the input sequence 142.

In some example embodiments, the protein design computation model 113 may modify the input sequence 142 by applying one or more energy-based models (EBMs). Accordingly, in some cases, the protein design computation model 113 may include one or more energy-based models (EBMs) 150 including, in the example shown in FIG. 1, a first energy-based model 150*a*, a second energy-based model 150*b*, and a third energy-based model 150*c*. Each of the energy-based models 150 may be trained to approximate the distribution (e.g., probability distribution) of a different set of protein sequences. For example, in some cases, the first energy-based model 150*a* may be trained to approximate a first distribution of protein sequence exhibiting a first property while the second energy-based model 150*b* may be trained to approximate a second distribution of protein sequences exhibiting a second property. In some cases, in addition to the first energy-based model 150*a* and the second energy-based model 150*b*, the protein design computation model 113 may further include the third energy-based model 150*c* trained to approximate a third distribution of protein sequences exhibiting a third property. In some cases, the output sequence 146 may be generated by applying, to the representation 144 of the input sequence 142, at least one of the energy-based models 150. As described in more details below, the input sequence 142 may be modified by applying a single energy-based model (EBM) such that the output sequence 146 exhibits the same property as the sample sequences used to train that energy-based model. Alternatively, the input sequence 142 may be modified by applying a composition of multiple energy-based models in order for the output sequence 146 to exhibit a combination of the properties exhibited by the sample sequences used to train the individual energy-based models.

Figure 2A:
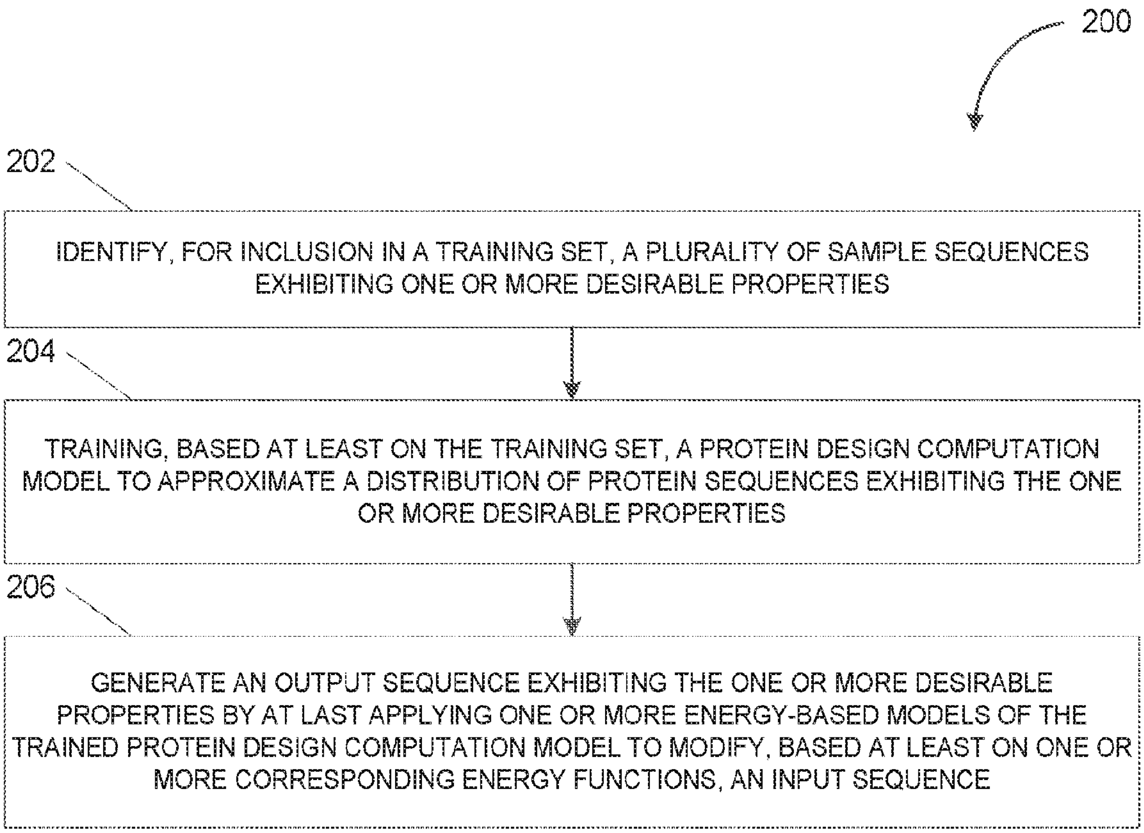
FIG. 2A depicts a flowchart illustrating an example of a process for generative protein design, in accordance with some example embodiments.

FIG. 2A depicts a flowchart illustrating an example of a process 200 for generative protein design, in accordance with some example embodiments. Referring to FIGS. 1 and 2A, the process 200 may be performed by the protein design engine 110 to train and apply the protein design computation model 113 to generate the output sequence 146 by at least modifying, over successive iterations, the representation 144 of the input sequence 142. As described in more detail below, in some cases, the protein design computation model 113 may include one or more energy-based models (EBMs), each of which being trained to approximate the distribution (e.g., probability distribution) of sample sequences that exhibit a different desirable property (e.g., expression, binding affinity, human-ness, non-immunogenicity, and/or the like) such that the output sequence 146 is generated to exhibit the same desirable properties.

At 202, the protein design engine 110 may identify, for inclusion in a training set, a plurality of sample sequences exhibiting one or more desirable properties. In some example embodiments, the protein design engine 110 may identify, for inclusion in each individual training set, sample sequences that exhibit certain desirable properties such as expression, binding affinity towards another molecule (e.g., a viral antigen, a tumor antigen, and/or the like), non-specificity, stability, immunogenicity, human-ness, self-association, and/or the like. In some cases, each plurality of sample sequences identified for inclusion in a training set may correspond to a subset of all known protein sequences selected based on the presence of certain desirable properties. For example, in some cases, the protein design engine 110 may identify, for inclusion in a first training set, a first plurality of sample sequences exhibiting a first property (e.g., expression). In some cases, the protein design engine 110 may generate additional training sets populated by sample sequences exhibiting other properties such as, for example, a second training set with a second plurality of sample sequences exhibiting a second property (e.g., binding affinity towards a target molecule), a third training set with a third plurality of sample sequences exhibiting a third property (e.g., non-immunogenicity), and/or the like. As described in more details below, the protein design engine 110 may train, based at least on the training sets, the protein design computation model 113 to approximate the distribution (e.g., probability distribution) of the sample sequences in each training set such that the trained protein design computation model 113 is able to modify the input sequence 142 to generate the output sequence 146 to exhibit at least one of corresponding desirable properties.

At 204, the protein design engine 110 may train, based at least on the training set, the protein design computation model 113 to approximate a distribution of protein sequences exhibiting the one or more desirable properties. In some example embodiments, the protein design computation model 113 may include the one or more energy-based models 150, each of which being trained to approximate the distribution of the sample sequences in a corresponding training set. For example, in some cases, the first energy-based model 150*a* may be trained, based at least on the first training set, to approximate a first distribution of protein sequences exhibiting the first property (e.g., expression). Furthermore, in some cases, the second energy-based model 150*b* may be trained to approximate a second distribution of protein sequences exhibiting the second property while the third energy-based model 150*c* may be trained to approximate a third distribution of protein sequences exhibiting the third property. As described in more details below, in some cases, the first energy-based model 150*a* may be applied to modify the input sequence 142 (e.g., the representation 144 of the input sequence 142) such that the output sequence 146 generated therefrom also exhibits the first property. Alternatively, in some cases, the first energy-based model 150*a* may be combined with at least one of the second energy-based model 150*b* and the third energy-based model 150*c* such that the input sequence 142 is modified, based on a composition of two or more energy-based models, to generate the output sequence 146 to exhibit two or more corresponding properties.

In some example embodiments, the training of each energy-based model (EBM) may include determining a corresponding energy function parameterized by the parameters of the energy-based model. For example, in cases where the first energy-based model 150*a* is an artificial neural network (ANN), such as a convolutional neural network and/or the like, the training of the first energy-based model 150*a* may include determining a first energy function 155*a* parameterized by the parameters (e.g., weights, biases, and/or the like) of the artificial neural network (ANN). Likewise, if the second energy-based model 150*b* is also an artificial neural network (e.g., a convolutional neural network and/or the like), the training of the second energy-based model 150*b* may include determining a second energy function 155*b* parameterized by the parameters (e.g., weights, biases, and/or the like) of the artificial neural network (ANN).

In some example embodiments, the protein design engine 110 may train each energy-based model (EBM) by performing gradient based Markov Chain Monte Carlo (MCMC) sampling, such as Langevin Markov Chain Monte Carlo sampling and/or the like, to approximate the gradient of the corresponding energy function. For example, in some cases, the training of the first energy-based model 150*a* may include gradient based Markov Chain Mote Carlo (MCMC) to approximate the gradient of the first energy function 155*a*. As will be described in more detail below, the gradient based Markov Chain Monte Carlo may include adjusting, over successive iterations, the parameters of the first energy-based model 155*a* (e.g., the weights and/or biases of the artificial neural network) to increase the similarity between the output sequences generated the first energy-based model 155*a* and the sample sequences in the first training set. Doing so may be tantamount to learning the distribution (e.g., probability distribution) of the sample sequences in the first training set such that the first energy function 155*a* provides a density estimation in which the sample sequences in the first training set occupy the higher density regions of the distribution. That is, a first sequence sampled from a higher density region of the distribution may be more likely to be within the distribution of the sample sequences than a second sequence sampled from a lower density region of the distribution Sampling from the distribution (e.g., probability distribution) may be guided by the first energy function 155*a*, particularly the gradient of the first energy function 155*a*, towards the higher density regions of the distribution populated by the sample sequences in the first training set. Accordingly, once trained, the first energy-based model 150*a* may model a distribution (e.g., a probability distribution) in which the likelihood of the sample sequences in the first training set is increased (or maximized). Moreover, the first energy function 155*a* may assign, to each sequence of amino acid residues, a value (e.g., an energy value) indicative of the likelihood of the sequence being in the distribution of the sample sequences in the first training set. For instance, the first energy function 155*a* may assign, to the first sequence, a lower value (e.g., a lower energy value) than the second sequence to indicate that the first sequence is more likely to be in the distribution of the sample sequences in the first training set than the second sequence.

In some example embodiments, the distribution (e.g., probability distribution) of the sample sequences in the first training set may correspond to the likelihood of different possible permutations of amino acid residues forming the sample sequences in the first training set. As noted, in some cases, this distribution may be a joint distribution (e.g., joint probability distribution) of all different possible permutations of amino acid residues forming the sample sequences in the first training set. For example, if the sample sequences in the first training set are n-length protein sequences containing up to an n-quantity of amino acid residues ($a_1$, $a_2$, . . . , $a_n$), the distribution (e.g., probability distribution) of the sample sequences in the first training set may correspond to the joint distribution across every possible permutation of an n-length sequence in which with each position can be occupied by one of twenty canonical amino acid residues, plus a gap character if the sample sequences are rendered in fixed-length representations. It should be appreciated that this joint distribution (e.g., joint probability distribution) may be a multidimensional probability distribution (e.g., n-dimensional probability distribution). Moreover, this joint distribution (e.g., joint probability distribution) may encode the marginal distributions of each of the n positions in the sample sequences as well as a variety of conditional distributions, such as the probability of a first position in a sample sequence being occupied by a first type of amino acid residue if a second position in the sample sequence is occupied by a second type of amino acid residue. As described in more detail below, the joint distribution (e.g., joint probability distribution) across every possible permutation of an n-length protein sequence may give rise to intractable computations given the length of typical protein sequences. For instance, the likelihood of a particular protein sequence within the joint distribution may be determined by computing the integral of a joint probability density function (PDF) characterizing the joint distribution. This computation may be intractable for high-dimensional joint probability distributions, as is the case for the large values of n associated with even average length protein sequences. For sequences of antibodies, n may be upwards of 149, meaning that the joint distribution (e.g., joint probability distribution) across sample antibody sequences may be a 149-dimensional probability distribution, which cannot be computed directly through integration. Instead, in some cases, the joint probability (e.g., joint probability distribution) of the sample sequences in the first training set may be approximated through Markov Chain Monte Carlo (MCMC) sampling including, for example, gradient based Markov Chain Monte Carlo (MCMC) sampling such as Markov Chain Monte Carlo sampling with Langevin dynamics (or Langevin Markov Chain Monte Carlo).

In some example embodiments, the first energy-based model 150*a* may be trained to approximate the distribution (e.g., probability distribution) of the sample sequences in the first training set through gradient based Markov Chain Monte Carlo sampling (e.g., Langevin Markov Chain Monte Carlo sampling) to increase (or maximize) the likelihood of the sample sequences in the first training set. For n-length protein sequences, which may include gap characters in the case of the aforementioned fixed-length representation, the resulting first energy-based model 150*a* may approximate the n-dimensional joint probability distribution of the n-length protein sequences. For a particular protein sequence, the corresponding first energy function 155*a* may also approximate this n-dimensional joint probability distribution by assigning a value (e.g., an energy value) indicative of the probability of the specific permutation of amino acid residues forming that protein sequence given what is observed across the sample sequences in the training set. The value assigned by the first energy function 155*a* may be lower for low energy configurations, which in this context are permutations of amino acid residues more similar to that of the sample sequences in the first training set and thus more likely to be in the distribution (e.g., probability distribution) of protein sequences exhibiting the first property. Alternatively, the value assigned by the first energy function 155*a* may be higher for high energy configurations, which are permutations of amino acid residues less similar to the sample sequences in the first training set and thus less likely to be in the corresponding distribution (e.g., probability distribution). The gradient of the first energy function 155*a*, which captures the change in energy value, may guide subsequent sequence generation towards sampling from the higher density regions of the distribution (e.g., probability distribution) over successive iterations such that the output sequences generated therefrom are increasingly similar to the sample sequences in the first training set and more likely to exhibit the same first property as those sample sequences.

At 206, the protein design engine 110 may generate an output sequence exhibiting the one or more desirable properties by at least applying one or more energy-based models (EBMs) of the trained protein design computation model 113 to modify, based at least on one or more corresponding energy functions, an input sequence. In some example embodiments, the first energy-based model 150*a* may be applied, either individually or in combination with at least one of the second energy-based model 150*b* and the third energy-based model 150*c*, to generate the output sequence 146 by sampling from the corresponding distributions (e.g., probability distributions). For example in some cases, the output sequence 146 may be generated by modifying the input sequence 142, which may be accomplished through operating on the representation 144 of the input sequence 142. In some cases, the output sequence 146 may be generated through Markov Chain Monte Carlo (MCMC) sampling (e.g., gradient based Markov Chain Monte Carlo and/or the like), which may include modifying the input sequence 142 over successive iterations to incrementally increase the likelihood of the output sequence 146 generated therefrom being within the distribution (e.g., probability distribution) of the corresponding sample sequences. Accordingly, in some cases, sampling from the distribution approximated by the first energy-based model 150*a*, for example, may include successively modifying the input sequence 142 based on the gradient of the first energy function 155*a* such that the output sequence 146 generated at each iteration is assigned a lower value (e.g., lower energy value) by the first energy function 155*a* than the output sequence 146 generated during one or more previous iterations. In this manner, the input sequence 142 may be modified over successive iterations, with each iteration further lowering the value (e.g., energy value) assigned by the first energy function 155*a* to indicate a greater likelihood of the corresponding output sequence 146 being within the distribution (e.g., probability distribution) of protein sequences exhibiting the first property.

Figure 2B:
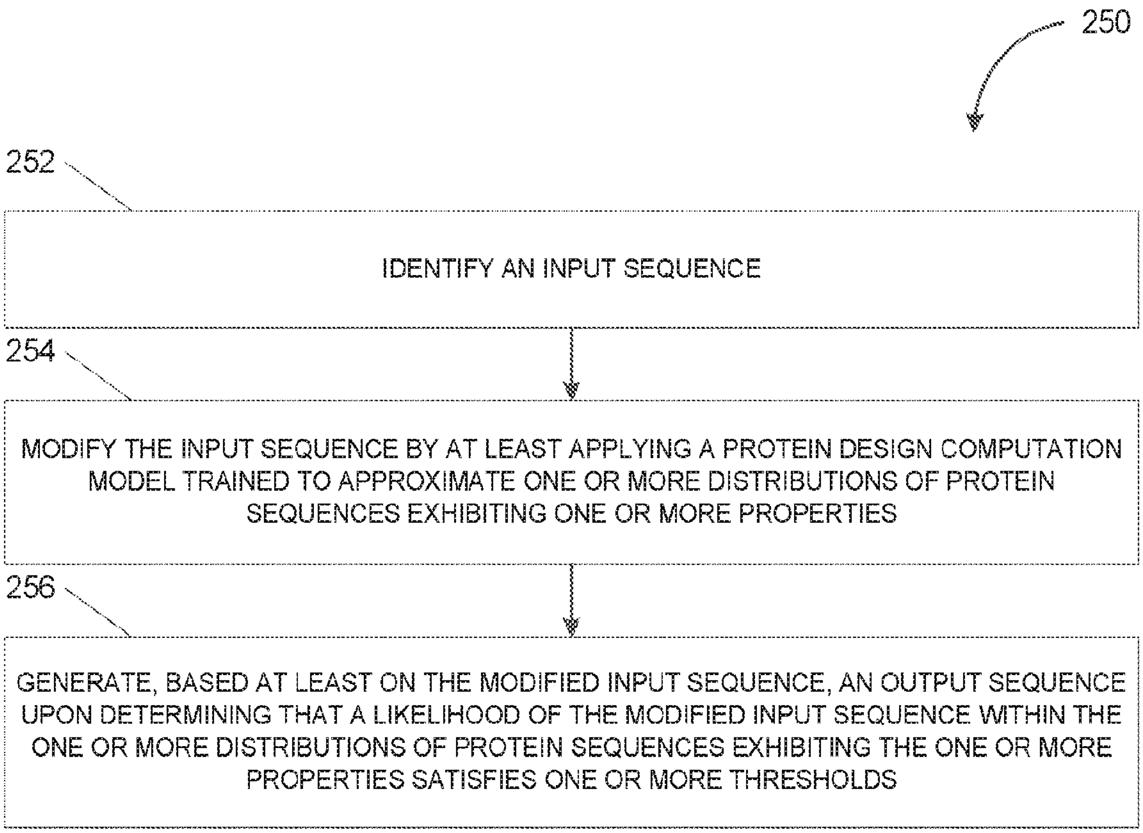
FIG. 2B depicts a flowchart illustrating another example of a process for generative protein design, in accordance with some example embodiments.

FIG. 2B depicts a flowchart illustrating an example of a process 250 for generative protein design, in accordance with some example embodiments. Referring to FIGS. 1 and 2A-B, the process 250 may be performed by the protein design engine 110 to apply, subsequent to training, the protein design computation model 113 to generate the output sequence 146 by at least modifying, over successive iterations, the representation 144 of the input sequence 142. In some cases, the process 250 may implement operation 206 of the process 200 shown in FIG. 2A. As described in more detail below, in some cases, the protein design computation model 113 may include one or more energy-based models (EBMs) and one or more corresponding energy functions, each of which being trained to approximate the distribution (e.g., probability distribution) of sample sequences that exhibit a different desirable property (e.g., expression, binding affinity, human-ness, non-immunogenicity, and/or the like). The output sequence 146 may be generated by applying the one or more energy-based models to modify, based at least on the one or more corresponding energy functions, the input sequence 142 (e.g., the representation 144 of the input sequence 142).

At 252, the protein design engine 110 may identify an input sequence. In some example embodiments, the protein design engine 110 may identify a noise sequence (e.g., a randomly ordered sequence of amino acid residues without known properties) without any known properties to serve as the input sequence 142. Alternatively, in some cases, the protein design engine 110 may identify a known protein sequence to serve as the input sequence 142. In those instances, the known protein sequence may be selected based on the presence of one or more properties. For example, in some cases, the known protein sequence may correspond to a non-human animal antibody identified through an immunization campaign as exhibiting one or more desirable properties (e.g., affinity). As described in more details below, the generative protein design process, which modifies the input sequence 142, may be performed to preserve, increase, or maximize one or more desirable properties present in the input sequence 142. Alternatively and/or additionally, the generative protein design process may include modifying the input sequence 142 to reduce or eliminate one or more undesirable properties present in the input sequence 142.

At 254, the protein design engine 110 may modify the input sequence by at least applying a protein design computation model trained to approximate one or more distributions of protein sequences exhibiting one or more properties. In some example embodiments, in order to generate the output sequence 146, the protein design engine 110 may apply the protein design computation model 113 to modify the input sequence 142 (e.g., the representation 144 of the input sequence 142). In some cases, the protein design computation model 113 may be trained to approximate one or more distributions of protein sequences exhibiting one or more desirable properties. For example, in some cases, the protein design computation model 113 may include the first energy-based model 150*a* trained to approximate the first distribution of protein sequences exhibiting the first property, the second energy-based model 150*b* trained to approximate the second distribution of protein sequences exhibiting the second property, and the third energy-based model 150*c* trained to approximate the third distribution of protein sequences exhibiting the third property. It should be appreciated that the input sequence 142 (e.g., the representation 144 of the input sequence 142) may be modified by applying the first energy-based model 150*a*, the second energy-based model 150*b*, and/or the third energy-based model 150*c*. For instance, in cases where the output sequence 146 is being generated to exhibit the first property, the first energy-based model 150*a* may be applied to modify the input sequence 142 (e.g., the representation 144 of the input sequence 142). In cases where the output sequence 146 is further being generated to exhibit the second property in addition to the first property, the second energy-based model 150*b* may also be applied to further modify the input sequence 142 (e.g., the representation 144 of the input sequence 142).

In some example embodiments, the protein design computation model 113 may modify the input sequence 142 (e.g., the representation 144 of the input sequence 142) over one or more successive iterations. For example, in some cases, the output sequence 146 may be generated through Markov Chain Monte Carlo (MCMC) sampling meaning that the input sequence 142 (e.g., the representation 144 of the input sequence 142) may be modified, incrementally over one or more successive iterations, while guided by one or more energy functions (e.g., the gradient of the one or more energy functions). That is, while an energy-based model trained to approximate a particular distribution of protein sequences is applied to modify the input sequence 142 (e.g., the representation 144 of the input sequence 142), the corresponding energy function may be applied to determine the likelihood of the resulting modified input sequence 142 within that distribution of protein sequences. For example, while the first energy-based model 150*a* is applied to modify the input sequence 142 (e.g., the representation 144 of the input sequence 142), each successive modification made to the input sequence 142 may be performed based on the first energy function 155*a* in order to increase the likelihood of the modified input sequence 142 being within the first distribution of protein sequences exhibiting the first property. As described in more details below, in instances where the output sequence 146 is being generated to exhibit the first property and the second property, a composition of the first energy-based model 150*a* and the second energy-based model 150*b* may be applied to modify the input sequence 142 over successive iterations. In some cases, the input sequence 142 may be modified based on a sum of the values (e.g., energy values) assigned, to the corresponding output sequence 146 at each iteration, by the first energy function 155*a* and the second energy function 155*b* to incrementally increase the likelihood of the output sequence 146 being within the distribution (e.g., probability distribution) of protein sequences exhibiting both the first property and the second property.

In some example embodiments, the modification made to the input sequence 142 during each successive iteration may be limited to certain portions of the input sequence 142 such that some portions of the input sequence 142 remains unchanged throughout the generative process. For example, in some cases, a first portion of the input sequence 142 may be associated with one or more desirable properties (e.g., affinity). Alternatively and/or additionally, a second portion of the input sequence 142 may be associated with one or more undesirable properties (e.g., immunogenicity). As such, in some cases, the second portion of the input sequence 142 may be masked to indicate that modifications to the input sequence 142 should be limited to the second portion of the input sequence 142 while the first portion of the input sequence 142, which remains unmasked, is preserved (or unchanged) throughout the generative process. In this context, the second portion of the input sequence 142 may be masked by populating the corresponding positions in the input sequence 142 with a masked character instead of the an amino acid residue to identify these positions as being open to modifications during the generative process. Doing so may preserve the one or more desirable properties associated with the first portion of the input sequence 142 while reducing (or eliminating) the one or more undesirable properties associated with the second portion of the input sequence 142 in the output sequence 146 generated therefrom. For instance, in some cases, the protein design engine 110 may generate the output sequence 146 by modifying the framework region of the input sequence 142 in order to increase the human-ness and reducing the immunogenicity of the input sequence 142. Furthermore, the protein design engine 110 may generate the output sequence 146 without modifying the complementarity determining regions (CDRs) of the input sequence 142 in order to preserve the binding affinity of the input sequence 142.

At 256, the protein design engine 110 may generate, based at least on the modified input sequence, an output sequence upon determining that a likelihood of the modified sequence within the one or more distribution of protein sequences exhibiting the one or more properties satisfies one or more thresholds. In some example embodiments, upon satisfaction of one or more criteria, the protein design engine 110 may generate the output sequence 146 based on the modified input sequence 142. For example, as described in more details below, the protein design computation model 113 may operate on the representation 144 of the input sequence 142, in which case the output sequence 146 may be generated based on the modified representation 144 of the input sequence 142. In some cases, the one or more aforementioned criteria may include that the modified input sequence 142 having a threshold likelihood of being within the distribution of protein sequences exhibiting one or more desirable properties. That is, the modification of the input sequence 142 (e.g., the representation 144 of the input sequence 142) may continue until the modified input sequence 142 achieves a threshold likelihood of being within the distribution of protein sequences having the first property, the second property, and/or the third property. It should be appreciated that other criteria may also be applied including a threshold iteration of modifications. For instance, in some cases, the protein design engine 110 may continue to apply the trained protein design computation model 113 to modify the input sequence 142 (e.g., the representation 144 of the input sequence 142) until a threshold quantity of iterations have been performed.

Figure 3:
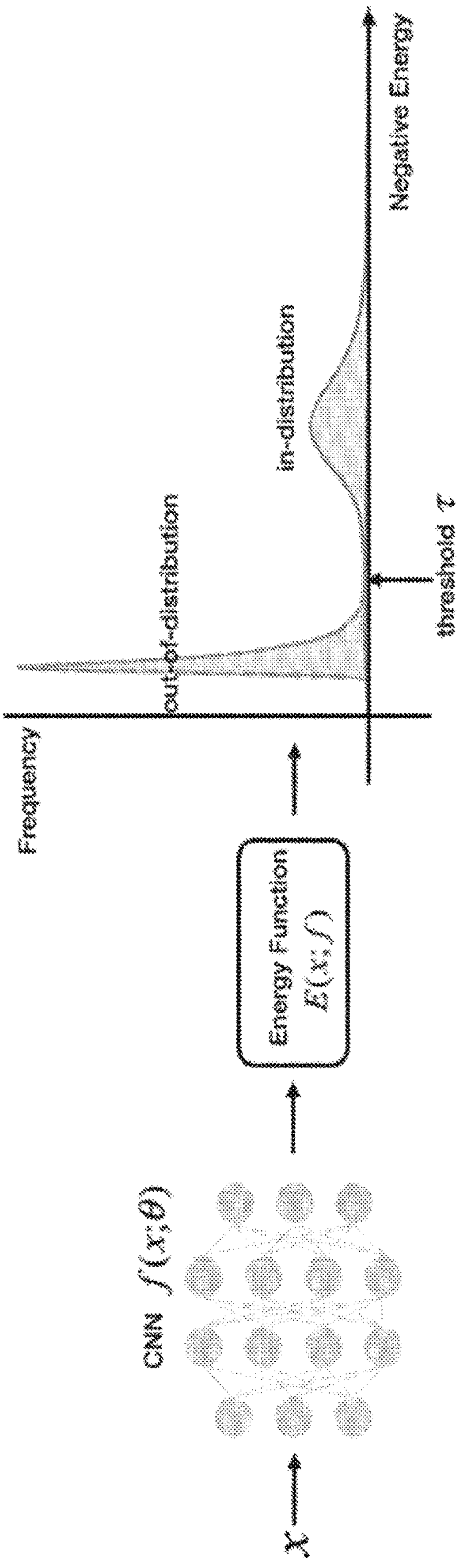
FIG. 3 depicts a schematic diagram illustrating an example of an energy-based model (EBM) and the corresponding energy function, in accordance with some example embodiments.

To further illustrate the distribution of protein sequences being approximated by an energy-based model and the corresponding energy function, FIG. 3 depicts a schematic diagram illustrating an example of an energy-based model (EBM) and the corresponding energy function, in accordance with some example embodiments. In the example shown in FIG. 3, the energy-based model f(x; θ) is a convolutional neural network (CNN) while the corresponding energy function is denoted as $E_\theta(x)$. In some cases, the energy function $E_\theta(x)$ may map an input x, which in this case is a protein sequence (or a specific permutation of amino acid residues), to a scalar "energy" value indicative of the likelihood of each protein sequence x in the distribution (e.g., probability distribution) of sample sequences used to train the energy-based model f(x; θ). As indicated by Equation (1) below, once the energy-based model f(x; θ) is trained, the energy function $E_\theta(x)$ may approximate a distribution (e.g., probability distribution) $p_\theta(x)$ akin to the Boltzmann distribution $e^{-E_\theta(x)}$, meaning that lower energy configurations of the protein sequences x are associated with a lower energy value indicative of a higher likelihood of occurrence within the distribution $p_\theta(x)$.

$$p_\theta(x) \propto e^{-E_\theta(x)} \tag{1}$$

In some cases, the energy-based model f(x; θ) may be trained based on a training set of sample sequences exhibiting one or more desirable properties. Furthermore, in some cases, the energy-based model f(x; θ) may be trained via contrastive divergence with sequences being drawn, over successive iterations, from the distribution $p_\theta(x)$ by Markov-Chain Monte Carlo (MCMC). Each draw from the distribution $p_\theta(x)$, which may include modifying an input sequence that could either be a known protein sequence or a noise sequence, yields a modified sequence with an incrementally lower energy configuration than ones from previous draws. In this context, it should be appreciated that a lower energy configuration is a permutation of amino acid residues that is more similar to those observed in the sample sequences. In the case of gradient based Markov Chain Monte Carlo (e.g., Langevin Markov Chain Monte Carlo (MCMC)) sampling, which is expressed in Equation (2) below, a subsequent iteration of refinement may include further modifying a previously modified sequence with a lower energy configuration from previous iterations.

$$x = x^{k-1} - \frac{\delta}{2}\nabla_x E_\theta\left(x^{k-1}\right) + \omega^k,\ \omega \sim N\left(0,\ \sigma^2\right) \tag{2}$$

wherein k denotes the k-th sampling iteration, δ is the step size, and the noise ω added to each sequence is drawn from a normal distribution with zero mean and variance σ.

Equation (3) shows that, in some cases, the training of the energy-based model f(x; θ) may include increasing (or maximizing) the log-likelihood of the sample sequences under the model. With this objective, the energy-based model f(x; θ) may aim to decrease the energy of the sample sequences in the training set, $y^-$, while increasing the energy of other sequences, $y^+$. Thus, when the energy-based model f(x; θ) is trained, the energy function $E_\theta(x)$ may output a lower energy value for a first sequence that is within the distribution (e.g., probability distribution) of the sample sequences in the training set than for a second sequence that is outside of the distribution of the sample sequences in the training set. An additional $L^2$-norm penalty may be added to the loss to regularize the energies. As shown in FIG. 3, once the energy-based model f(x; θ) is trained, the energy function $E_\theta(x)$ may perform out-of-distribution detection (ODD). That is, given a threshold τ, a protein sequence x may be in the distribution of the sample sequences in the training set if the energy function $E_\theta(x)$ assigns a value (e.g., energy value) that satisfies the threshold τ. Contrastingly, the protein sequence x may be out of the distribution of the sample sequences in the training set if the energy function $E_\theta(x)$ assigns a value (e.g., energy value) that fails to satisfy the threshold τ.

$$E_{y\sim p}[\log \log p_\theta(y)] = E_{y^-\sim p_\theta}[f_\theta(y^-)] - E_{y^+\sim p}[f_\theta(y^+)] \tag{3}$$

Figure 4:
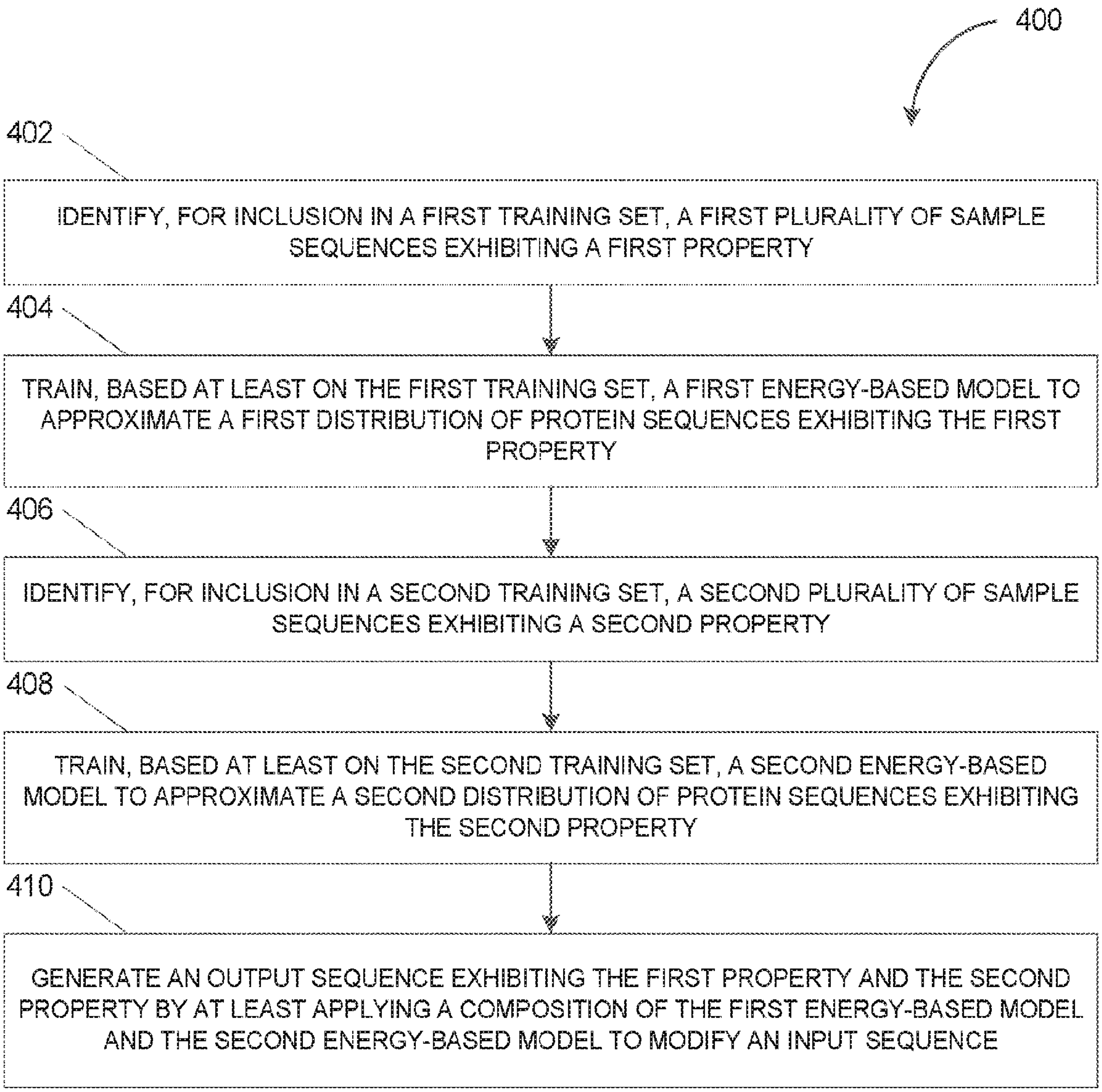
FIG. 4 depicts a flowchart illustrating another example of a process for generative protein design, in accordance with some example embodiments.

FIG. 4 depicts a flowchart illustrating another example of a process 400 for generative protein design, in accordance with some example embodiments. Referring to FIGS. 1 and 4, the process 400 may be performed by the protein design engine 110 to modify, over successive iterations, the input sequence 142 (e.g., the representation 144 of the input sequence 142) to generate the output sequence 146 to exhibit multiple desirable properties. As described in more details below, in some cases, the protein design computation model 113 may include multiple energy-based models, each of which being trained to approximate the distribution (e.g., probability distribution) of sample sequences that exhibit a desirable property (e.g., expression, binding affinity, human-ness, non-immunogenicity, and/or the like). Accordingly, in some cases, a composition of multiple energy-based models may be applied to modify the input sequence 142 (e.g., the representation 144 of the input sequence 144) based on a combination of the corresponding energy-functions. In some cases, the modifications are made over successive iterations. Doing so may increase (or maximize) the likelihood of the resulting output sequence 146 in the distribution (e.g., probability distribution) of protein sequences exhibiting the corresponding combination of desirable properties.

At 402, the protein design engine 110 may identify, for inclusion in a first training set, a first plurality of sample sequences exhibiting a first property. For example, in some cases, the protein design engine 110 may identify a first plurality of sample sequences exhibiting a desirable property such as expression, binding affinity towards another molecule (e.g., a viral antigen, a tumor antigen, and/or the like), non-specificity, stability, immunogenicity, human-ness, self-association, and/or the like. In some cases, the first plurality of sample sequences may include some but not all of the know protein sequences such that a less time and computational resources may be expended to train a less structurally complex energy-based model to approximate its distribution (e.g., probability distribution). For instance, by limiting training to a subset of all known protein sequences, the energy-based model may be implemented with fewer parameters than typical large language models (LLMs) and trained to achieve state of-the-generative performance (or better than state-of-the-art generative performance) in less time and with less computational resources.

At 404, the protein design engine 110 may train, based at least on the first training set, a first energy-based model to approximate a first distribution of protein sequences exhibiting the first property. For example, in some cases, the protein design engine 110 may train, based at least on a first training set of sample sequences exhibiting a first property, the first energy-based model 150*a* to approximate the first distribution (e.g., first probability distribution) of protein sequences exhibiting the first property. In some cases, the first energy-based model 150*a* may be trained, through Markov Chain Monte Carlo sampling, to approximate the first distribution (e.g., first probability distribution) of protein sequences exhibiting the first property. Accordingly, in some cases, the training of the first energy-based model 150*a* may include applying the first energy-based model 150*a* to sample from the first distribution (e.g., first probability distribution) of protein sequences exhibiting the first property and adjusting the first energy-based model 150*a* to sample from the higher density regions of the first distribution (e.g., first probability distribution), which are occupied by the protein sequences exhibiting the first property. As described in more details below, the first distribution (e.g., first probability distribution) of protein sequences exhibiting the first property may be approximated when the first energy-based model 150*a* is trained to generate output sequences with sufficient similarities to the sample sequences in the first training set. In some cases, the first energy-based model 150*a* may be trained when the difference (e.g., Kullback-Leibler divergence and/or the like) between the distribution of output sequences generated by the first energy-based model 150*a* and the distribution of the sample sequences in the first training set satisfies one or more thresholds.

In some example embodiments, the training of the first energy-based model 150*a* may include modifying the input sequence 142 (e.g., the representation 144 of the input sequence 142). This operation may be tantamount to drawing a single sample from the first distribution (e.g., first probability distribution) of protein sequences exhibiting the first property. However, before the first energy-based model 150*a* reaches a trained state, the sample may be drawn from a lower density region of the first distribution (e.g., first probability distribution) of protein sequences exhibiting the first property, meaning that the output sequence 146 at this stage may not be sufficiently similar to the sample sequences in the first training set to also exhibit the first property. Accordingly, the training of the first energy-based model 150*a* may include multiple iterations of sampling in order to sample from incrementally higher density regions in the first distribution (e.g., first probability distribution) of protein sequences exhibiting the first property. For example, in some cases, the training of the first energy-based model 150*a* may include adjusting one or more parameters (e.g., weights, biases, and/or the like) of the first energy-based model 150*b* to increase the similarity between the sample sequences in the first training set and the output sequence 146 generated by the modifying of the input sequence 142. This may be done over successive iterations, with each iteration being a sample draw that includes additional modifications of the input sequence 142 and further adjustments to the parameters of the first energy-based model 150*a* to incrementally increase the similarity between the sample sequences in the first training set and the output sequence 146 generated by the modifying of the input sequence 142. Again, as noted, increasing the similarity between the output sequence 146 and the sample sequences in the first training set may be tantamount to sampling from higher density regions in the first distribution (e.g., first probability distribution) of protein sequences exhibiting the first property. Where the first energy-based model 150*a* is trained via Langevin Markov Chain Monte Carlo, the modifications made to the input sequence 142 may be cumulative over successive iterations, with each iteration of modifications yielding a modified sequence that is more similar to the sample sequences in the first training set. In particular, multiple modified sequences being generated during each iteration, for example, by modifying the input sequence 142 (e.g., the representation 144 of the input sequence 142), such that a subsequent iteration of modifications is made to a previously modified sequence with a greater similarity to the sample sequences in the first training set than the other previously modified sequences.

At 406, the protein design engine 110 may identify, for inclusion in a second training set, a second plurality of sample sequences exhibiting a second property. For example, in some cases, the protein design engine 110 may identify a second plurality of sample sequences exhibiting a different desirable property than the first plurality of sample sequences in the first training set. Accordingly, the first training set and the second training set may include sample sequences that exhibiting a different one of expression, binding affinity towards another molecule (e.g., a viral antigen, a tumor antigen, and/or the like), non-specificity, stability, immunogenicity, human-ness, self-association, and/or the like. As with the first plurality of sample sequences in the first training set, the second plurality of training sequences in the second training set may include some but not all of the know protein sequences in order to reduce the architectural complexity (e.g., quantity of parameters) in the energy-based model (EBM) needed to model the underlying distribution (e.g., probability distribution). Limiting training to the subset of known protein sequence exhibiting the second property may also reduce the time and computational resources required to train the energy-based model to achieve state of-the-generative performance (or better than state-of-the-art generative performance).

At 408, the protein design engine 110 may train, based at least on the second training set, a second energy-based model to approximate a second distribution of protein sequences exhibiting the second property. For example, in some cases, the protein design engine 110 may train, based at least on the second training set of sample sequences exhibiting a second property, the second energy-based model 150*b* to approximate the second distribution (e.g., second probability distribution) of protein sequences exhibiting the second property. The second energy-based model 150*b* may be trained by at least applying the second energy-based model 150*b* to modify the input sequence 142 (e.g., the representation 144 of the input sequence 142) and adjusting one or more parameters (e.g., weights, biases, and/or the like) of the second energy-based model 150*b* to increase the similarity between the sample sequences in the second training set and the output sequence 146 generated by the modifying of the input sequence 142. In some cases, the second energy-based model 150*b* may be trained over successive iterations, with each subsequent iteration including additional modifications of the input sequence 142 and further adjustments to the parameters of the second energy-based model 150*b*. Doing so may engender, with each successive iteration, an incremental increase in the similarity between the sample sequences in the second training set and the output sequence 146 generated by the modifying of the input sequence 142. The second energy-based model 150*b* may be trained once the output sequence 146 generated by the second energy-based model 150*b* exhibits sufficient similarities to the sample sequences in the second training set. For instance, in some cases, the second energy-based model 150*b* may be trained the difference (e.g., Kullback-Leibler divergence and/or the like) between the distribution of output sequences generated by the second energy-based model 150*b* and the distribution of the sample sequences in the second training set satisfies one or more thresholds.

In some cases, training the second energy-based model 150*b* may include determining the second energy function 155*b*, which may be parameterized by the parameters (e.g., weights, biases, and/or the like) of the second energy-based model 150*b*. Once the second energy-based model 150*b* is trained, the second energy function 155*b* may output a value indicative of the likelihood of a sequence of amino acid residues within the distribution (e.g., probability distribution) of the sample sequences in the second training set. As the second energy-based model 150*b* is trained to increase (or maximize) the likelihood of the sample sequences in the second training set, the second energy function 155*b* may provide a density estimation of the distribution (e.g., probability distribution) of the sample sequences. In particular, training the second energy-based model 150*b* to generate output sequences that are similar to the sample sequences in the second training set may include determining the second energy function 155*b* to differentiate between high density regions and low density regions within the distribution of the sample sequences in the second training set. Accordingly, when the second energy-based model 150*b* is trained, the second energy function 155*b* may output values (e.g., energy values) indicative of whether a protein sequence is sampled from a high density region (e.g., in-distribution) or a low density region (e.g., out-of-distribution) of the distribution of the sample sequences in the second training set. As described in more details below, the values (e.g., energy values) output by the second energy function 155*b* may guide protein sequence generation towards sampling from higher density regions of the distribution populated by protein sequences with lower values (e.g., lower energy values) than the protein sequences in the lower density regions of the distribution.

At 410, the protein design engine 110 may generate an output sequence exhibiting the first property and the second property by at least applying a composition of the first energy-based model and the second energy-based model to modify an input sequence. In some example embodiments, once the first energy-based model 150*a* and the second energy-based model 150*b* are trained, the protein design engine 110 may apply a composition of the first energy-based model 150*a* and the second energy-based model 150*b* to generate the output sequence 146 to exhibit both the first property present in the sample sequences used to train the first energy-based model 150*a* and the second property present in the sample sequences used to train the second energy-based model 150*b*. As noted, the first energy-based model 150*a* may be trained to approximate the first distribution of protein sequences exhibiting the first property while the second energy-based model 150*b* may be trained to approximate the second distribution of protein sequences exhibiting the second property. In cases where the output sequence 146 is further desired to exhibit a third property in addition to the first property and the second property, the protein design engine 110 may apply a composition that further includes the third energy-based model 150*b* trained to approximate a third distribution of protein sequences exhibiting the third property.

In some example embodiments, the protein design engine 110 may generate the output sequence 146 to exhibit multiple properties, such as the first property and the second property, by sampling from the third distribution of protein sequences exhibiting both the first property and the second property. In some cases, the third distribution of protein sequences exhibiting the first property and the second property may be approximated by a combination of the first energy function 155*a* of the first energy-based model 150*a* and the second energy function 155*b* of the second energy-based model 150*b*. For example, in some cases, the generation of the output sequence 146 may be guided by a third value that combines (e.g., as a sum and/or the like) a first value (e.g., first energy value) output by the first energy function 155*a* and a second value (e.g., second energy value) output by the second energy function 155*b*. Changes in this third value may be representative of changes in the probability density of the third distribution of protein sequences that exhibit both the first property and the second property. Accordingly, in some cases, the generation of the output sequence 146 may include sampling, based on the changes in the third value, from the higher density regions of the third distribution occupied by protein sequences exhibiting the first property and the second property.

In some example embodiments, the protein design engine 110 may sample from the third distribution of protein sequences exhibiting both the first property and the second property by at least modifying, over multiple iterations, the input sequence 142 (e.g., the representation 144 of the input sequence 142). In instances where a first portion of the input sequence 142 is associated with a third property that is desirable to be present in the output sequence 146, the modifications to the input sequence 142 may be limited to a second portion of the input sequence 142 such that the first portion of the input sequence 142 remains unchanged throughout the generative process. Moreover, in some cases, the protein design engine 110 may perform Markov Chain Monte Carlo (MCMC) sampling, such as gradient based Markov Chain Monte Carlo sampling, in order to sample from the third distribution. Accordingly, in some cases, the modification of the input sequence 142 may be performed based on changes in the third value combining the first value output by the first energy function 155*a* and the second value output by the second energy function 155*b*. For example, each iteration of sequence generation may include modifying the input sequence 142 to increase the likelihood of the corresponding output sequence 146 being in the third distribution, as indicated by the change in the third value. For gradient based Markov Chain Monte Carlo (MCMC), such as Markov Chain Monte Carlo (MCMC) with Langevin dynamics, each successive iteration of sequence generation may include further modifying a modified sequence from a previous iteration having a higher likelihood of being within the third distribution than other previously modified sequences. For instance, during one iteration of sequence generation, the composition of the first energy-based model 150*a* and the second energy-based model 150*b* may be applied to modify the input sequence 142 to generate a first modified sequence and a second modified sequence. During a subsequent iteration of sequence generation, the composition of the first energy-based model 150*a* and the second energy-based model 150*b* may be applied to further modify the first modified sequence instead of the second modified sequence if the first modified sequence is more likely to be in the third distribution than the second modified sequence. In some cases, the input sequence 142 may be modified over a threshold quantity of iterations, after which point the resulting output sequence 146 may be proposed for further computational or experimental analysis. Alternatively and/or additionally, the protein design engine 110 may continue to modify the input sequence 142 until the likelihood of the resulting output sequence 146 being in the third distribution of protein sequences of exhibiting both the first property and the second property satisfies one or more thresholds.

To further illustrate, Equation (4) below indicates that a composition of two or more energy-based models may model the distribution p(x) of protein sequences having an i-quantity of properties ($c_1$ and $c_2, \ldots, c_i$). Like in the case of a single energy-based model, the distribution p(x) approximated by the composition of energy-based models may be the Boltzmann distribution $e^{-E_\theta(x|c_i)}$ in which lower energy configurations of protein sequences x are associated with a lower energy value indicative of a higher likelihood of occurrence within the distribution p(x). According to Equation (4), the composition of two or more energy-based models, each of which representative of the distribution (e.g., probability distribution) of protein sequences exhibiting a particular property, may correspond to the product of the individual likelihood of a single protein sequence exhibiting each property.

$$p(x \mid c_1 \text{ and } c_2, \ldots, c_i) = \prod_i p(x \mid c_i) \propto e^{-E_\theta(x|c_i)} \quad (4)$$

In some cases, the distribution of protein sequences having every one of the i-quantity of concepts may correspond to the sum of the distribution of protein sequences exhibiting each individual property $c_i$. Sampling from the distribution of protein sequences having all i-quantity of concepts may be performed in accordance with Equation (5) below with the noise ω added at each k-th sampling iteration corresponding to $\omega^k \sim \mathcal{N}(0, \lambda)$.

$$\tilde{x}^k = \tilde{x}^{k-1} - \frac{\lambda}{2}\nabla_x \sum_i E_\theta(\tilde{x}^{k-1}) + \omega^k \quad (5)$$

In some example embodiments, instead of generating the output sequence 146 to exhibit both the first property and the second property, the protein design engine 110 may apply a composition of the first energy-based model 150*a* and the second energy-based model 150*b* to generate the output sequence 146 to exhibit a disjunction of two or more properties (e.g., either the first property or the second property) or a negation of at least one property (e.g., the first property but not the second property). In instances where the output sequence 146 is generated to exhibit either the first property or the second property, the protein design engine 110 may apply a composition of the first energy-based model 150*a* and the second energy-based model 150*b* to sample from either the first distribution of protein sequences exhibiting the first property or the second distribution of protein sequences exhibiting the second property. That is, the output sequence 146 may be generated by sampling from a third probability distribution in which the high design regions are populated by protein sequences exhibiting either property and the low design regions are populated by protein sequences exhibiting neither properties. This may be approximated as the sum of the individual likelihood of a single protein sequence exhibiting each property. Accordingly, as shown in Equation (6) below, sampling from such a distribution may be accomplished by modifying the input sequence 142 (e.g., the representation 144 of the input sequence 142) based on at least on a third value that is the log-sum-exp of the first value output by the first energy function 155*a* and the second value output by the second energy function 155*b*.

$$p(x|c_1 \text{ or } c_2, \ldots, c_i) = \propto \sum_i \frac{p(x|c_i)}{Z(c_i)} \quad (6)$$

wherein $Z(c_i)$ denotes the partition function of each property, which may be assumed to be equal in order to render Equation (6) a tractable calculation.

Equation (7) below shows the simplification of Equation (6) with equal partition functions $Z(c_i)$. In Equation (7), the operation log sumexp($f_1, \ldots, f_{\mathcal{N}}$)=log $\Sigma_i$exp($f_i$). Sampling from the distribution, for example, via Markov Chain Monte Carlo (MCMC) with Langevin dynamics, may be performed in accordance with Equation (8) below.

$$\tilde{x}^k = \tilde{x}^{k-1} - \frac{\lambda}{2}\nabla_x \sum_i logsumexp(-E(x|c_1), -E(x|c_2), \ldots, -E(x|c_i)) + \omega^k \quad (8)$$

wherein the noise $\omega^k \sim \mathcal{N}(0, \lambda)$ is added to the sequence sampled from the distribution during the k-th iteration of Langevin Markov Chain Monte Carlo (MCMC) sampling.

In some example embodiments, the output sequence 146 may be generated to exhibit the second property but not the first property by the protein design engine 110 applying the composition of the first energy-based model 150*a* and the second energy-based model 150*b* to sample from a third probability distribution in which the high design regions are populated by protein sequences exhibiting the second property but not the first property and the low density regions are populated by protein sequences that either exhibit the first property or fails to exhibit the second property. As shown in Equation (9) below, this particular distribution may be approximated by the difference between the likelihood of a protein sequence not exhibiting the first property $c_1$ and the likelihood of a protein sequence exhibiting the second property $c_2$.

$$p\left(x|\text{not}(c_1), (c_2) = \frac{p(x|c_2)}{p(x|c_1)^{\alpha}} \propto e^{\alpha E(x|c_i) - E(x|c_2)} \right. \tag{9}$$

wherein α denotes a smoothing parameter serving as a regularizer, for instance, to prevent over- and underfitting. For example, the third distribution expressed in Equation (9) becomes a uniform distribution where α=0. According to Equation (10), Langevin Markov Chain Monte Carlo (MCMC) sampling may be performed to draw sequences from the third distribution, with $\omega^k \sim \mathcal{N}(0, \lambda)$ is added to the sequence sampled from the distribution during the k-th iteration.

$$\tilde{x}^k = \tilde{x}^{k-1} - \frac{\lambda}{2}\nabla_x\left(\alpha E(x|c_1) - E(x|c_2)\right) + \omega^k \tag{10}$$

Figure 5:
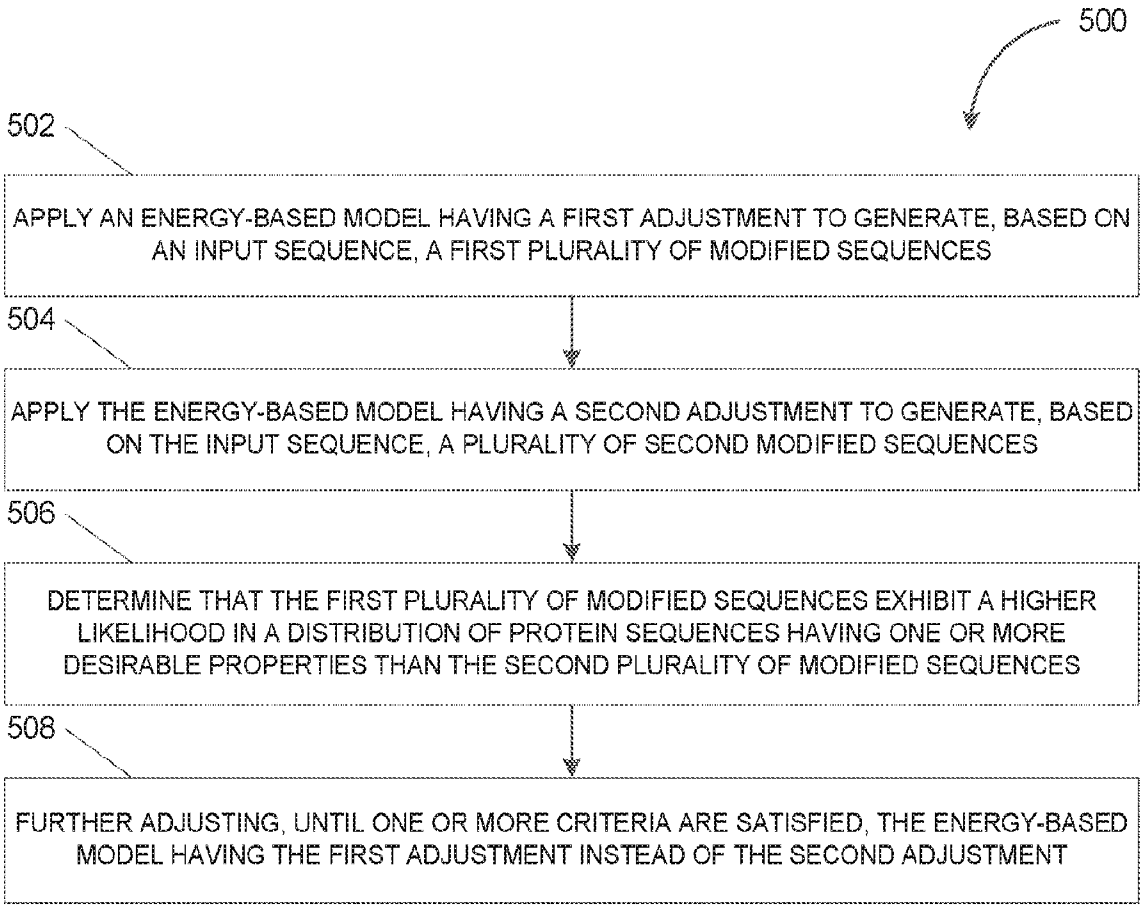
FIG. 5 depicts a flowchart illustrating an example of a process for training an energy-based model, in accordance with some example embodiments.

FIG. 5 depicts a flowchart illustrating an example of a process 500 for training an energy-based model (EBM) for protein sequence generation, in accordance with some example embodiments. Referring to FIGS. 1, 2A, and 4, the process 500 may be performed by the protein design engine 110 to train the protein design computation model 113 including, for example, each of the one or more energy-based models 150. In some cases, the process 500 may implement operation 204 of the process 200 shown in FIG. 2A or operations 404 and 408 of the process 400 shown in FIG. 4. In some cases, each of the one or more energy-based models 150 may be trained through Markov Chain Monte Carlo (MCMC), such as gradient based Markov Chain Monte Carlo, to model the distribution of protein sequences having one or more desirable properties. As described in more details below, the training of the one or more energy-based models 150 may include determining the corresponding energy functions 155 such that the energy functions 155 approximate the distribution of the protein sequences with the one or more desirable properties. Moreover, each of the one or more energy-based models 150 may be trained over multiple successive iterations, with each iteration further adjusting the parameters (e.g., weights, biases, and/or the like) of the one or more energy-based models 150.

At 502, the protein design engine 110 may apply an energy-based model having a first adjustment to generate, based on an input sequence, a first plurality of modified sequences. In some example embodiments, the protein design engine 110 may train each of the one or more energy-based models 150 included in the protein design computation model 113. For example, the first energy-based model 150*a* may be trained based on the first training set, which may include sample sequences exhibiting the first property. In some cases, training the first energy-based model 150*a* may include determining the corresponding first energy function 155*a*, which is parameterized by the parameters (e.g., weights, biases, and/or the like) of the first energy-based model 150*a*, to approximate the distribution (e.g., probability distribution) of protein sequences exhibiting the first property. Moreover, in some cases, the protein design engine 110 may train the first energy-based model 150*a* through Markov Chain Monte Carlo (MCMC) sampling, such as Markov Chain Monte Carlo (MCMC) sampling with Langevin dynamics.

In some example embodiments, training the first energy-based model 150*a* through Markov Chain Monte Carlo (MCMC) sampling may include applying, over successive iterations, incremental adjustments to the parameters (e.g., weights, biases, and/or the like) of the first energy-based model 150*a* to increase the likelihood of the output sequences generated by the first energy-based model 150*a* modifying the input sequence 142 (e.g., the representation 144 of the input sequence 142) in the distribution (e.g., probability distribution) of protein sequences exhibiting the first property. As described in more details below, the parameters (e.g., weights, biases, and/or the like) of the first energy-based model 150*a* may be adjusted to increase (or maximize) the conformity between the distribution (e.g., probability distribution) of the output sequences generated by the first energy-based model 150*a* and the distribution (e.g., probability distribution) of protein sequences exhibiting the first property. Doing so may increase (or maximize) the likelihood of the first property being present in the output sequences generated by the first energy-based model 150*a* at least because the first energy-based model 150*a* is sampling from the high density regions of the distribution populated by protein sequences having the first property including the sample sequences in the first training set.

In some example embodiments, a single iteration of adjustments may include the protein design engine 110 applying different adjustments to the first energy-based model 150*a*, with each one of the first energy-based model 150*a* having a different adjustment then applied to generate modified sequences. Furthermore, in some cases, the one of the first energy-based model 150*a* having an adjustment that yielded output sequences with a higher likelihood in the distribution of protein sequences exhibiting the first property may be selected for further adjustments during a subsequent iteration. For example, in some cases, the protein design engine 110 may apply the first energy-based model 150*a* having a first adjustment to generate a first plurality of modified sequence. In some cases, the first adjustment may include one or more changes to the parameters (e.g., weights, biases, and/or the like) of the first energy-based model 150*a*. During a subsequent iteration of adjustments, the protein design engine 110 may further adjust the first energy-based model 150*a* having the first adjustment if the output sequences generated by the first energy-based model 150*a* having the first adjustment exhibits of a higher likelihood within the distribution (e.g., probability distribution) of protein sequences having the first property than the output sequences generated by the first energy-based model 150*a* having a different adjustment.

At 504, the protein design engine 110 may apply the energy-based model having a second adjustment to generate, based on the input sequence, a second plurality of modified sequences. In some example embodiments, in addition to applying the first energy-based model 150*a* having the first adjustment to generate the first plurality of modified sequences, the protein design engine 110 may apply the first energy-based model 150*a* having a second adjustment to generate a second plurality of modified sequences. In some cases, the second adjustment may include one or more changes to the parameters (e.g., weights, biases, and/or the like) of the first energy-based model 150*a* that are different than the first adjustment. Accordingly, the first energy-based model 150*a* having the second adjustment may generate outputs sequences having a different distribution (e.g., probability distribution) than those generated by the first energy-based model 150*a* having the first adjustment. As described in more details below, if the first plurality of modified sequences generated by the first energy-based model 150*a* having the first adjustment exhibits a higher likelihood in the distribution (e.g., probability distribution) of protein sequences having the first property than the second plurality of modified sequences generated by the first energy-based model 150*b* having the second adjustment, the protein design engine 110 may further adjust the first energy-based model 150*a* having the first adjustment during a subsequent iteration of adjustments in order to further increase the likelihood of the output sequences generated by the first energy-based model 150*a* in the distribution (e.g., probability distribution) of protein sequences having the first property.

At 506, the protein design engine 110 may determine that the first plurality of modified sequences exhibit a higher likelihood of in a distribution of protein sequences having one or more desirable properties than the second plurality of modified sequences. In some example embodiments, the protein design engine 110 may select, for further adjustments during a subsequent iteration, the first energy-based model 150*a* having the first adjustment instead of the first energy-based model 150*b* having the second adjustment if the output sequences generated by the first energy-based model 150*a* having the first adjustment exhibit a higher likelihood in the distribution (e.g., probability distribution) of protein sequences exhibiting the first property than the output sequences generated by the first energy-based model 150*a* having the second adjustment. In some cases, the protein design engine 110 may select the first energy-based model 150*a* having the first adjustment for further adjusting during a subsequent iteration if a first distribution (e.g., first probability distribution) of the first plurality of modified sequences generated by the first energy-based model 150*a* having the first adjustment is less different to the distribution (e.g., probability distribution) of protein sequences having the first property than a second distribution (e.g., second probability distribution) of the second plurality of modified sequences generated by the first energy-based model 150*a* having the second adjustment. For example, in some cases, the protein design engine 110 may determine a first distance (e.g., Kullback-Leibler divergence and/or the like) between the first distribution (e.g., first probability distribution) of the first plurality of modified sequences generated by the first energy-based model 150*a* having the first adjustment and the distribution (e.g., probability distribution) of protein sequences having the first property. Furthermore, the protein design engine 110 may determine a second distance (e.g., Kullback-Leibler divergence and/or the like) between the second distribution (e.g., second probability distribution) of the second plurality of modified sequences generated by the first energy-based model 150*a* having the second adjustment and the distribution (e.g., probability distribution) of protein sequences having the first property. As described in more details below, the protein design engine 110 may select, based at least on the first distance and the second distance, the first energy-based model 150*a* having the first adjustment or the first energy-based model 150*b* having the second adjustment for further adjustment during a subsequent iteration.

At 508, the protein design engine 110 may further adjust, until one or more criteria are satisfied, the energy-based model having the first adjustment instead of the second adjustment. In some example embodiments, the protein design engine 110 may further adjust the first energy-based model 150*a* having the first adjustment instead of the second adjustment if the first distance is less than the second distance. For example, during a subsequent iteration of adjustments, the protein design engine 110 may make further adjustments to the parameters (e.g., weights, biases, and/or the like) the first energy-based model 150*a* having the first adjustments before applying the further adjusted first energy-based model 150*a* to generate additional modified sequences.

In some cases, further adjusting the parameters (e.g., weights, biases, and/or the like) of the first energy-based model 150*a* may further alter the distribution (e.g., probability distribution) of the output sequences generated by the first energy-based model 150*a*, for example, to increase (or maximize) the correspondence between the distribution (e.g., probability distribution) of the output sequences generated by the first energy-based model 150*a* and that of protein sequences having the first property. For example, in some cases, the parameters of the first energy-based model 150*a* may be further adjusted to decrease (or minimize) the distance (e.g., Kullback-Leibler divergence and/or the like) of the distribution (e.g., probability distribution) of the output sequences of the first energy-based model 150*a* relative to the distribution (e.g., probability distribution) of protein sequences exhibiting the first property. Accordingly, in some cases, the first energy-based model 150*a* having the first adjustment may undergo one or more additional iterations of further adjustments until the protein design engine 110 determines that one or more criteria have been satisfied. For instance, in some cases, the protein design engine 110 may perform one or more additional iterations of further adjustments until a threshold quantity of iterations of adjustments have been performed. Alternatively and/or additionally, the protein design engine 110 may perform one or more additional iterations of further adjustments until the correspondence (e.g., the distance (e.g., Kullback-Leibler divergence and/or the like)) between the distribution of the output sequences generated by the first energy-based model 150*a* and the distribution of the protein sequences having the first property satisfies one or more thresholds. Once the one or more criteria are satisfied, the first energy-based model 150*a* may be applied to sample from the high density regions of the distribution (e.g., probability distribution), which are populated by protein sequences exhibiting the first property, such that the output sequence 146 generated therefrom also exhibits the first property.

Figure 6A:
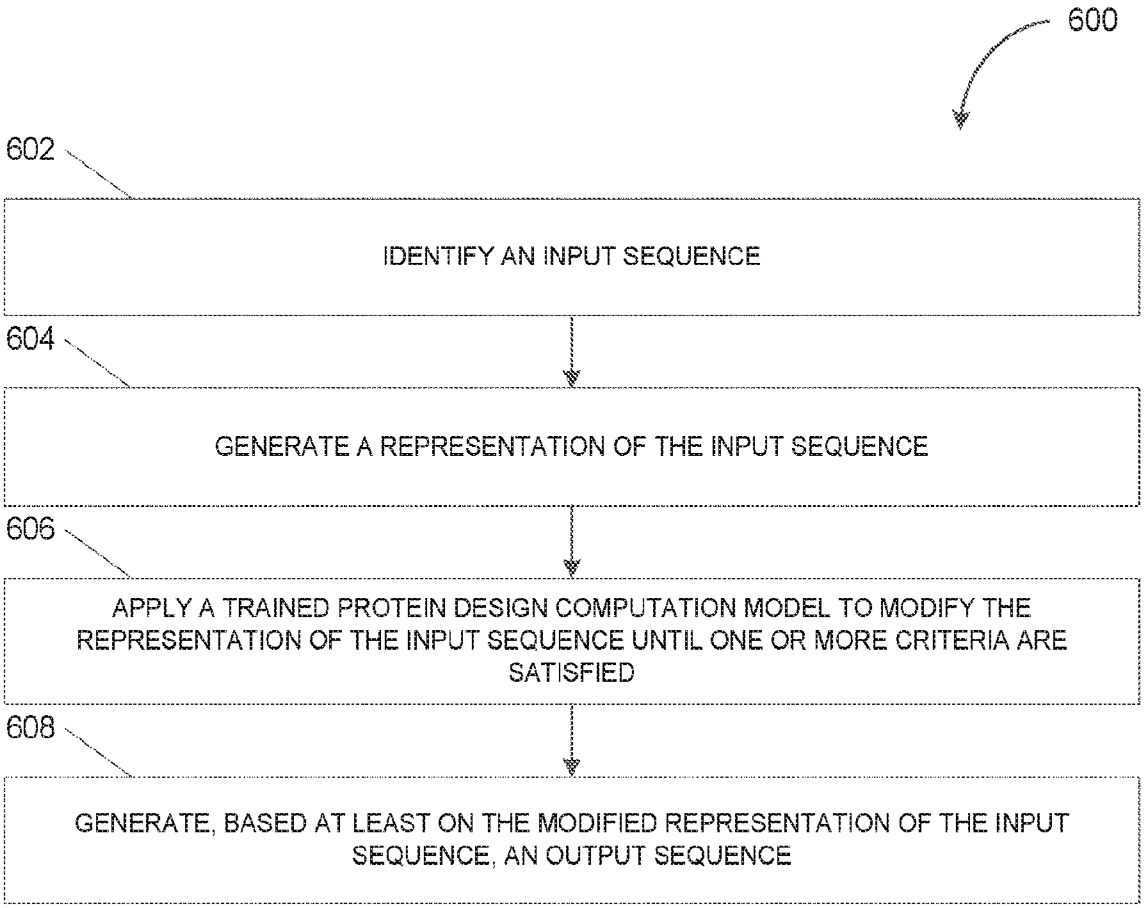
FIG. 6A depicts a flowchart illustrating another example of a process for generative protein design, in accordance with some example embodiments.

FIG. 6A depicts a flowchart illustrating an example of a process 800 for generative protein design, in accordance with some example embodiments. Referring to FIGS. 1, 2A, 4, and 6A, the process 800 may be performed by the protein design engine 110. In some cases, the process 800 may be performed by the protein design engine 110 to implement, for example, operation 206 of the process 200 shown in FIG. 2A and operation 410 of the process 400 shown in FIG. 4. As described in more details below, the process 400 may include the protein design engine 110 operating on the representation 144 of the input sequence 142 instead of directly on the input sequence 142. Doing so may increase the computational efficiency of the generative protein design process at least because the representation 144 may better accommodate modifications to the input sequence 142 that changes the length of the input sequence 142.

At 602, the protein design engine 110 may identify an input sequence. In some example embodiments, the protein design engine 110 may identify a known protein sequence or a noise sequence (e.g., a randomly ordered sequence of amino acid residues without known properties) to serve as the input sequence 142. In instances where the input sequence 142 is a known protein sequence, the protein design engine 110 may select the known protein sequence based on one or more properties present in the known protein sequence. For example, in some cases, the known protein sequence may correspond to a non-human animal antibody identified through an immunization campaign as exhibiting one or more desirable properties (e.g., affinity). As described in more details below, the generative protein design process, which modifies the input sequence 142, may be performed to preserve, increase, or maximize one or more desirable properties present in the input sequence 142. Alternatively and/or additionally, the generative protein design process may include modifying the input sequence 142 to reduce or eliminate one or more undesirable properties present in the input sequence 142.

At 604, the protein design engine 110 may generate a representation of the input sequence. In some example embodiments, the protein design engine 110 may generate the representation 144 of the input sequence 142 by applying a structural role based numbering scheme and assigning, to each amino acid residue in the input sequence 142, an integer position in the fixed length sequence. In some cases, the integer position assigned to an amino acid residue present in the input sequence 142 may be selected from a range of integers, such as [1, 149]), corresponding to the structural role of that amino acid residue. At any position in the fixed length sequence where the input sequence 142 lacks an amino acid residue having the corresponding structural role, the representation 144 may be generated to include a gap character to indicate the absence of an amino acid residue at that position. As described in more details below, the protein design engine 110 may generate the output sequence 146 by operating on the representation 144 of the input sequence 142 instead of directly on the input sequence 142.

At 606, the protein design engine 110 may apply a trained protein design computation model to modify the representation of the input sequence until one or more criteria are satisfied. In some example embodiments, the protein design engine 110 may apply the protein design computation model 113, which includes the one or more energy-based models 150, to modify the representation 144 of the input sequence 142 over one or more successive iterations. As noted, the representation 144 may include, at one or more positions, a gap character to indicate the absence of an amino acid residue having a corresponding structural role. Accordingly, in some cases, modifications that alter the length of the input sequence 142, such as the insertion and deletion of an amino acid residue, may be accomplished by swapping in or out a gap character in the representation 144 of the input sequence 142. For example, to insert an amino acid residue at an empty position in the input sequence 142, the protein design computation model 113 may replace a corresponding gap character with an amino acid residue (e.g., one of the twenty canonical amino acid residues). Alternatively, to delete the amino acid residue occupying a position in the input sequence 142, the protein design computation model 113 may replace the amino acid residue with a gap character to indicate the absence of an amino acid residue having the corresponding structural role in that position.

As noted, the protein design computation model 113 may be applied to modify the representation 144 of the input sequence 142 over multiple successive iterations until one or more criteria are satisfied. For instance, in some cases, the protein design computation model 113 may be applied to continue modifying the representation 144 of the input sequence 142 until a threshold quantity of iterations of modifications have been performed. Alternatively and/or additionally, the protein design computation model 113 may be applied to continue modifying the representation 144 of the input sequence 142 until the likelihood of the resulting output sequence 146 in the distribution (e.g., probability distribution) of protein sequences having the one or more desirable properties satisfy one or more thresholds. In some cases, the protein design computation model 113 may limit the modifications to certain portions of the representation 144 of the input sequence 142. For example, in some cases, the framework regions in the representation 144 of the input sequence 142 may be masked (e.g., with masked tokens) to limit the modifications to the framework regions of the input sequence 142 and prevent any modifications to the complementarity determining regions (CDRs) of the input sequence 142. Moreover, in some cases, a single iteration of modifications may include the protein design computation model 113 generating multiple modified sequences, each of which having a different modification, before the one modified sequence having a higher likelihood in the distribution of protein sequence having one or more desirable properties is selected for further modifications during a subsequent iteration. It should be appreciated that each iteration of modifications may be tantamount to drawing multiple samples from a distribution (e.g., probability distribution) of protein sequences, with each successive iteration drawing samples from a higher density region of the distribution (e.g., probability distribution) populated by protein sequences exhibiting the one or more desirable properties.

At 608, the protein design engine 110 may generate, based at least on the modified representation of the input sequence, an output sequence. In some example embodiments, after the representation 144 of the input sequence 142 has undergone one or more successive iterations of modifications by the protein design computation model 113, the protein design engine 110 may generate the output sequence 146 to correspond to the modified representation 144 of the input sequence 142. In some cases, the representation 144 of the input sequence 142 may include, at each position in the modified representation 144 of the input sequence 142 absent an amino acid residue having a corresponding structural role, a gap character to indicate the absence of the amino acid residue. Accordingly, in some cases, the protein design engine 110 may generate the output sequence 146 by at least removing, from the modified representation 144 of the input sequence, the one or more gap characters present therein.

Figure 6B:
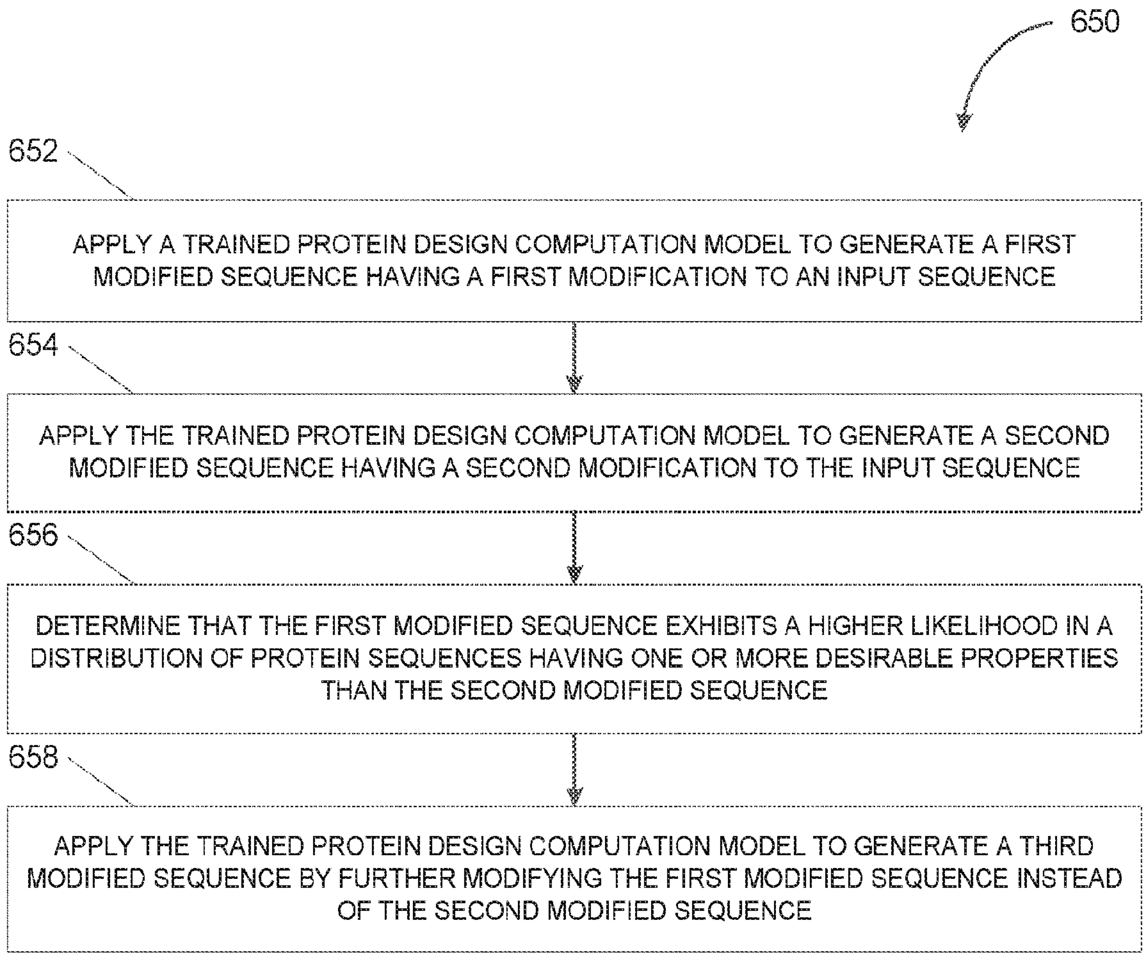
FIG. 6B depicts a flowchart illustrating an example of a process for generative protein design with gradient based Markov Chain Monte Carlo (MCMC), in accordance with some example embodiments.

FIG. 6B depicts a flowchart illustrating an example of a process 850 for generative protein design, in accordance with some example embodiments. Referring to FIGS. 1 and 6A, the process 850 may be performed by the protein design engine 110 to generate the output sequence 146 to exhibit one or more desirable properties by applying one or more of the energy-based models 150 to sample, over multiple iterations, from a distribution (e.g., probability distribution) of protein sequences exhibiting the one or more desirable properties. As described in more details below, each sampling iteration may include further modifying a previously modified sequence with a greater similarity to the sample sequences in the first training set than the other previously modified sequences. As such, the input sequence 142 (e.g., the representation 144 of the input sequence 142) may be modified, over successive iterations, to increase (or maximize) the likelihood of the output sequence 146 generated therefrom in the distribution (e.g., probability distribution) of protein sequences exhibiting the one or more desirable properties.

At 652, the protein design engine 110 may apply a trained protein design computation model to generate a first modified sequence having a first modification to an input sequence. In some example embodiments, the protein design engine 110 may generate the first modified sequence having the first modification by at least applying one or more of the energy-based models 150 included in the protein design computation model 113 to modify the input sequence 142 (e.g., the representation 144 of the input sequence 142). For example, in some cases, the protein design engine 110 may generate the first modified sequence by applying the first energy-based model 150*a* to modify the input sequence 142 (e.g., the representation 144 of the input sequence 142), an operation that may be tantamount to sampling from the first distribution of protein sequences exhibiting the first property. Alternatively and/or additionally, the protein design engine 110 may generate the first modified sequence by applying the second energy-based model 150*b* to modify the input sequence 142 (e.g., the representation 144 of the input sequence 142), which may be tantamount to sampling from the second distribution of protein sequences exhibiting the second property. In some cases, the input sequence 142 may be modified by one or more of inserting an amino acid residue, deleting an amino acid residue, and changing the identity of an amino acid residue in the input sequence 142. In instances where the protein design engine 110 generates the first modified sequence based on a composition of the first energy-based model 150*a* and the second energy-based model 150*b*, the first modified sequence may be sampled from the third distribution of protein sequences exhibiting the first property and the second property.

At 654, the protein design engine 110 may apply the trained protein design computation model to generate a second modified sequence having a second modification to the input sequence. In some example embodiments, the protein design engine 110 may generate the second modified sequence having the second modification by at least applying one or more of the energy-based models 150 included in the protein design computation model 113 to modify the input sequence 142 (e.g., the representation 144 of the input sequence 142). For example, in some cases, the protein design engine 110 may apply the first energy-based model 150*a* and/or the second energy-based model 150*b* to modify the input sequence 142 (e.g., the representation 144 of the input sequence 142). Doing so may include sampling the second modified sequence from a different region of the corresponding distribution (e.g., probability distribution) than the first modified sequence. Accordingly, in some cases, the second modified sequence may exhibit a lower (or higher) likelihood of being in the distribution of protein sequences exhibiting the first property and/or the second property than the second modified sequence, for example, by being less (or more) similar to the sample sequences in the training sets used to train the first energy-based model 150*a* and/or the second energy-based model 150*b*. As described in more details below, where the protein design engine 110 generates the output sequence 146 through gradient based Markov Chain Monte Carlo (MCMC), such as Langevin Markov Chain Monte Carlo, the protein design engine 110 may continue to modify the input sequence 142 (e.g., the representation 144 of the input sequence 142) by applying the first energy-based model 150*a* and/or the second energy-based model 150*b* to further modify one of the first modified sequence and the second modified sequence that is sampled from a higher density region of the corresponding distribution (e.g., probability distribution).

At 656, the protein design engine 110 may determine that the first modified sequence exhibits a higher likelihood in a distribution of protein sequences having one or more desirable properties than the second modified sequence. In some example embodiments, the protein design engine 110 may determine that the first modified sequence exhibits a higher likelihood in the distribution of protein sequences exhibiting the first property and/or the second property than the second modified sequence if the first modified sequence is associated with a lower value (e.g., energy value) than the second modified sequence. For example, in instances where the first energy-based model 150*a* is being applied to sample from the first distribution of protein sequences exhibiting the first property, the protein design engine 110 may apply the first energy function 155*a* to determine a value (e.g., energy value) indicative of a first likelihood of a modified sequence in the first distribution of protein sequences having the first property. Alternatively, if the protein design engine 110 is applying the second energy-based model 150*b* to sample from the second distribution of protein sequences exhibiting the second property, the protein design engine 110 may apply the second energy function 155*b* to determine a value (e.g., energy value) indicative of a second likelihood of the modified sequence in the second distribution of protein sequences. In instances where a composition of the first energy-based model 150*a* and the second energy-based model 150*b* is applied to sample from the third distribution of protein sequences exhibiting the first property and the second property, the protein design engine 110 may apply a combination of the first energy function 155*a* and the second energy function 155*b* to determine a value indicative of a third likelihood of the modified sequence in the third distribution of protein sequences having the first property and the second property.

In cases where the first modified sequence is associated with a first value that is lower than a second value of the second modified sequence, the protein design engine 110 may determine that the first modified sequence is sampled from a higher density region of the distribution (e.g., probability distribution) of protein sequences having one or more desirable properties than the second modified sequence. Subsequent sampling iterations may cumulate modifications to the input sequence 142 that sample from incrementally higher density regions of the distribution. That is, in some cases, instead of each sampling iteration initiating a new input sequence, successive sampling iterations may operate on a previously modified sequence having a lower value (e.g., energy value) than the other previously modified sequences. Accordingly, as described in more details below, the protein design engine 110 may continue to sample from the higher density region of the distribution including by further modifying, based on the first energy function 155*a* and/or the second energy function 155*b*, the first modified sequence instead of the second modified sequence during one or more subsequent sampling iterations.

At 658, the protein design engine 110 may apply the trained protein design computation model to generate a third modified sequence by further modifying the first modified sequence instead of the second modified sequence. In some example embodiments, the protein design engine 110 may generate a third modified sequence by further modifying, based at least on the output of the first energy function 155*a* and/or the second energy function 155*b*, the first modified sequence instead of the second modified sequence. In some cases, the protein design engine 110 may apply the first energy-based model 155*a*, the second energy-based model 155*b*, or a composition of the two to further modify the first modified sequence if the first energy function 155*a* and/or the second energy function 155*b* outputs a lower value (e.g., lower energy value) for the first modified sequence than the second modified sequence, which indicates that the first modified sequence was sampled from a higher density region of the corresponding distribution than the second modified sequence. Accordingly, applying the first energy-based model 150*a* and/or the second energy-based model 150*b* to further modify the first modified sequence may be tantamount to sampling the third modified sequence from an even higher density region of the corresponding distribution than the first modified sequence.

In view of the above-described implementations of subject matter this application discloses the following list of examples, wherein one feature of an example in isolation or more than one feature of said example taken in combination and, optionally, in combination with one or more features of one or more further examples are further examples also falling within the disclosure of this application:

Item 1: A computer-implemented method, comprising: identifying an input sequence; modifying the input sequence by at least applying a protein design computation model trained to approximate a first distribution of protein sequences exhibiting the first property, the protein design computation model including a first energy-based model (EBM) and or a first energy function, and the protein design computation model modifying of the input sequence by at least applying the first energy-based model (EBM) to modify the input sequence, and applying the first energy function to determine a first likelihood of the modified input sequence within the first distribution of protein sequences exhibiting the first property; and generating, based at least on the modified input sequence, an output sequence upon determining that the first likelihood of the modified input sequence within the first distribution of protein sequences exhibiting the first property satisfies one or more thresholds.

Item 2: The method of Item 1, wherein the first energy function is parameterized by a plurality of parameters comprising the first energy-based model (EBM).

Item 3: The method of any of Items 1 to 2, wherein the input sequence is modified based at least on an output of the first energy function such that each modification increases the first likelihood of the modified input sequence generated therefrom being within the first distribution of protein sequences exhibiting the first property.

Item 4: The method of any of Items 1 to 3, wherein the generating of the output sequence includes: applying, to the input sequence, a first modification to generate a first modified input sequence; applying, to the input sequence, a second modification to generate a second modified input sequence; applying the first energy function to determine, for each of the first modified input sequence and the second modified input sequence, a respective likelihood of the first modified input sequence and the second modified input sequence being within the first distribution of protein sequences exhibiting the first property; and further modifying, based at least on the respective likelihood of each of the first modified input sequence and the second modified input sequence being within the first distribution, one of the first input modified sequence and the second input modified sequence.

Item 5: The method of any of Items 1 to 4, wherein the first distribution of protein sequences exhibiting the first property comprises a probability distribution that includes, for each position within a fixed-length sequence, a probability of each possible amino acid residue occupying that position.

Item 6: The method of any of Items 1 to 5, wherein the protein design computation model is further trained to approximate a second distribution of protein sequences exhibiting a second property.

Item 7: The method of Item 6, wherein the training of the protein design computation model includes adjusting a plurality of parameters of a second energy-based model (EBM) such that a second energy function parameterized by the plurality of parameters outputs an energy value corresponding to a second likelihood of a sequence within the second distribution of protein sequences.

Item 8: The method of any of Items 6 to 7, wherein the input sequence is modified by at least applying a composition of the first energy-based model (EBM) and the second energy-based model (EBM) representative of a third distribution of protein sequences exhibiting the first property and the second property.

Item 9: The method of any of Items 6 to 8, wherein the input sequence is modified based at least on a combination of the first energy function and the second energy function.

Item 10: The method of any of Items 6 to 9, wherein the modifying of the input sequence further includes: applying the second energy-based model (EBM) to further modify the input sequence; applying the second energy function to determine a second likelihood of the further modified input sequence within the second distribution of protein sequences exhibiting the second property; and generating, based at least on the further modified input sequence, the output sequence upon determining that a sum the first likelihood of the further modified input sequence within the first distribution of protein sequences and the second likelihood of the further modified input sequence within the second distribution of protein sequences satisfies one or more thresholds.

Item 11: The method of Item 10, wherein the sum corresponds to a third likelihood of the modified input sequence within a third distribution of protein sequences exhibiting the first property and the second property.

Item 12: The method of Item 11, wherein the input sequence is modified based on the sum of the first likelihood and the second likelihood such that each modification increases the third likelihood of the modified input sequence within the third distribution of protein sequences exhibiting the first property and the second property.

Item 13: The method of any of Items 10 to 12, wherein the modifying of the input sequence further includes: generating a first modified input sequence having a first modification to the input sequence; determining, based at least on a combination of the first energy function and the second energy function, a first energy value indicative of a third likelihood of the first modified input sequence within a third distribution of protein sequences exhibiting the first property and the second property; generating a second modified input sequence having a second modification to the input sequence; determining, based at least on the combination of the first energy function and the second energy function, a second energy value indicative of the third likelihood of the second modified input sequence within the third distribution of protein sequences exhibiting the first property and the second property; and further modifying, based at least on a comparison of the first energy value and the second energy value, one of the first modified input sequence and the second modified input sequence.

Item 14: The method of Item 13, wherein the first modified input sequence is further modified instead of the second modified input sequence based at least on the first energy value of the first modified input sequence being lower than the second energy value of the second modified input sequence.

Item 15: The method of any of Items 6 to 14, wherein the first property and the second property comprise a different one of expression, binding affinity towards another molecule, non-specificity, stability, immunogenicity, humanness, and self-association.

Item 16: The method of any of Items 6 to 15, wherein the protein design computation model is further trained to approximate a third distribution of protein sequences exhibiting a third property.

Item 17: The method of Item 16, wherein the training of the protein design computation model includes adjusting a plurality of parameters of a third energy-based model (EBM) such that a third energy function parameterized by the plurality of parameters outputs an energy value corresponding to a third likelihood of a sequence within the third distribution of protein sequences.

Item 18: The method of any of Items 16 to 17, wherein the input sequence is modified by at least applying a composition of the first energy-based model (EBM), the second energy-based model (EBM), and the third energy-based model (EBM), and wherein the output sequence is generated based on the modified input sequence upon determining that a sum of a respective likelihood of the modified input sequence within the first distribution of protein sequences, the second distribution of protein sequences, and the third distribution of protein sequences satisfies the one or more thresholds.

Item 19: The method of any of Items 1 to 18, further comprising: generating a fixed-length representation of the input sequence; and applying the first energy-based model (EBM) to modify the fixed-length representation of the input sequence.

Item 20: The method of Item 19, wherein the fixed-length representation of the input sequence includes a gap character at each position in the input sequence without an amino acid residue having a structural role associated with the position.

Item 21: The method of any of Items 19 to 20, wherein the modifying of the input sequence includes changing an identity of an amino acid residue at one or more positions within the fixed-length representation of the input sequence.

Item 22: The method of any of Items 19 to 21, wherein the modifying of the input sequence includes at least one of deleting an amino acid residue occupying a position within the fixed-length representation of the input sequence by at least replacing the amino acid residue with a gap character, and inserting an amino acid residue at a position within the fixed-length representation of the input sequence by at least replacing a gap residue occupying the position with the amino acid residue.

Item 23: The method of any of Items 1 to 22, further comprising: identifying a plurality of sample sequences exhibiting the first property; and training of the protein design computation model by at least adjusting one or more parameters of the first energy-based model to increase a similarity between one or more sequences output by the first energy-based model (EBM) and the plurality of sample sequences.

Item 24: The method of Item 23, wherein the plurality of sample sequences comprises a subset of known protein sequences that excludes one or more known protein sequences failing to exhibit the first property.

Item 25 The method of any of Items 23 to 24, wherein the training of the protein design computation model includes adjusting the one or more parameters of the first energy-based model (EBM) to increase the first likelihood of a sequence generated by the first energy-based model within the first distribution of protein sequences exhibiting the first property.

Item 26: The method of any of Items 23 to 25, wherein the training of the protein design computation model includes adjusting the one or more of parameters of the first energy-based model (EBM) such that the first energy function parameterized by the one or more parameters outputs a lower energy value for a first sequence that is within the first distribution of protein sequences than for a second sequence that is outside of the first distribution of protein sequences.

Item 27: The method of any of Items 1 to 26, wherein the first-energy based model is an artificial neural network (ANN).

Item 28: The method of any of Items 1 to 27, further comprising: determining, within the input sequence, an adjustable segment and a fixed segment; and applying the first energy-based model (EBM) to modify the adjustable segment but not the fixed segment of the input sequence.

Item 29: The method of Item 28, wherein the adjustable segment includes a crystallizable fragment (Fc) of an antibody having the input sequence.

Item 30: The method of any of Items 28 to 29, wherein the fixed segment includes an antigen binding fragment (Fab), a variable fragment (Fv), a complementarity determining region (CDR), and/or a Vernier zone of an antibody having the input sequence.

Item 31: A computer-implemented method, comprising: identifying a first plurality of sample sequences exhibiting a first property; training, based at least on the first plurality of sample sequences, a protein design computation model to approximate a first distribution of protein sequences exhibiting the first property, the training of the protein design computation model includes adjusting a first plurality of parameters of a first energy-based model (EBM) to increase a first similarity between one or more first sequences output by the first energy-based model (EBM) and the first plurality of sample sequences exhibiting the first property, and determining a first energy function parameterized by the first plurality of parameters to output a first energy value corresponding to a first likelihood of the one or more first sequences within the first distribution of protein sequences exhibiting the first property; and generating an output sequence exhibiting the first property by at least applying the first energy-based model (EBM) of the trained protein design computation model to modify, based at least on the first energy function, an input sequence.

Item 32: The method of Item 31, further comprising: identifying a second plurality of sample sequences exhibiting a second property; further training, based at least on the second plurality of sample sequences, the protein design computation model to approximate a second distribution of protein sequences exhibiting the second property, the further training of the protein design computation model includes adjusting a second plurality of parameters of a second energy-based model (EBM) to increase a second similarity between one or more second sequences output by the second energy-based model (EBM) and the second plurality of sample sequences exhibiting the second property, and determining a second energy function parameterized by the second plurality of parameters to output a second energy value corresponding to a second likelihood of the one or more second sequences within the second distribution of protein sequences exhibiting the second property.

Item 33: The method of Item 32, wherein the generating of the output sequence includes: applying the first energy-based model (EBM) and the second energy-based model (EBM) to modify the input sequence; applying the first energy function to determine, for the modified input sequence, the first energy value indicative of the first likelihood of the modified input sequence within the first distribution of protein sequences exhibiting the first property; applying the second energy function to determine, for the modified input sequence, the second energy value indicative of the second likelihood of the modified input sequence within the second distribution of protein sequences exhibiting the second property; and generating, based at least on the modified input sequence, an output sequence upon determining that a sum of the first energy value and the second energy value satisfies one or more thresholds.

Item 34: The method of Item 33, wherein the first property and the second property comprise a different one of expression, binding affinity towards another molecule, non-specificity, stability, immunogenicity, human-ness, and self-association.

Item 35: The method of any of Items 31 to 34, wherein the first plurality of sample sequences comprise a subset of known protein sequences that excludes one or more known protein sequences failing to exhibit the first property.

Item 36: The method of any of Items 31 to 35, wherein the training of the protein design computation model includes: applying the first energy-based model (EBM) having a first adjustment to generate a first plurality of modified sequences; applying the first energy-based model (EBM) having a second adjustment to generate a second plurality of modified sequences; determining that the first plurality of modified sequences is more similar to the first plurality of sample sequences than the second plurality of modified sequences; and in response to determining that the first plurality of modified sequences is more similar to the first plurality of sample sequences than the second plurality of modified sequences, further training the protein design computation model by applying a third adjustment to the first energy-based model (EBM).

Item 37: The method of Item 36, wherein each of the first adjustment and the second adjustment include a change to one or more weights and/or biases of the first energy-based model (EBM).

Item 38: The method of any of Items 31 to 37, wherein the first energy-based model modifies the input sequence based on an output of the first energy function such that each modification increases the first likelihood of the modified input sequence generated therefrom being within the first distribution of protein sequences exhibiting the first property.

Item 39: A system, comprising: at least one data processor; and at least one memory storing instructions, which when executed by the at least one data processor, result in operations comprising the method of any of Items 1 to 30 or the method of any of Items 31 to 38.

Item 40: A non-transitory computer readable medium storing instructions, which when executed by at least one data processor, result in operations comprising the method of any of Items 1 to 30 or the method of any of Items 31 to 38.

Figure 7:
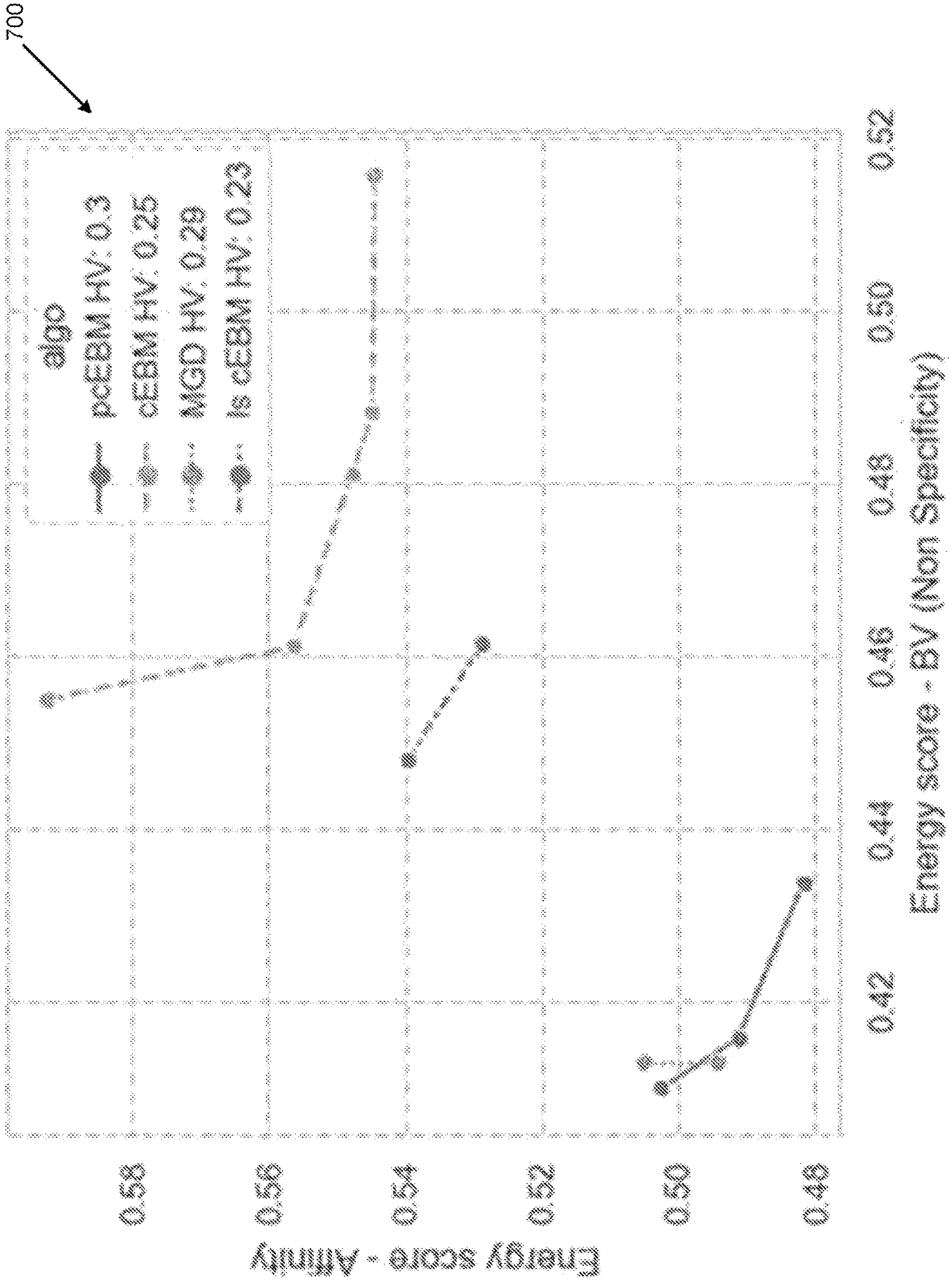
FIG. 7 depicts a graph illustrating a comparison of the combination of properties present in the protein sequences generated by different protein design techniques, in accordance with some example embodiments.

FIG. 7 depicts a graph 700 illustrating a comparison of the combination of properties present in the protein sequences generated by different protein design techniques including an example implementation of protein design computation model 113, in accordance with some example embodiments. As shown in FIG. 7, each protein sequence may be plotted in the graph 700 based on its level of binding specificity (along the x-axis) and binding affinity (along the y-axis). The combination of properties exhibited by each protein sequence, in this case binding affinity and binding specificity, is compared based on the hypervolume (HV) of enclosed by the protein sequences generated by different protein design techniques including an example implementation of the protein design computation model 113. The other protein design techniques shown in FIG. 7 are compositional energy-based model (cEBM) in which plain gradient descent is performed instead of multiple gradient descent, linearly scaled compositional energy-based model (1s cEBM) in which each energy function is scaled then summed for subsequent gradient based Markov Chain Monte Carlo (MCMC), and multiple gradient descent (MGD) in which multiple gradient descent is used for multi-objective optimization (MOO) instead of sampling from multiple energy functions. As shown in FIG. 7, pareto-compositional energy-based model (pcEBM), an example implementation of the protein design computation model 113 in which multiple gradient descent from multiple energy functions modeling different properties are applied for gradient based Markov Chain Monte Carlo (MCMC), generated protein sequences with a better combination of binding affinity and binding specificity than other protein design techniques.

Figure 8:
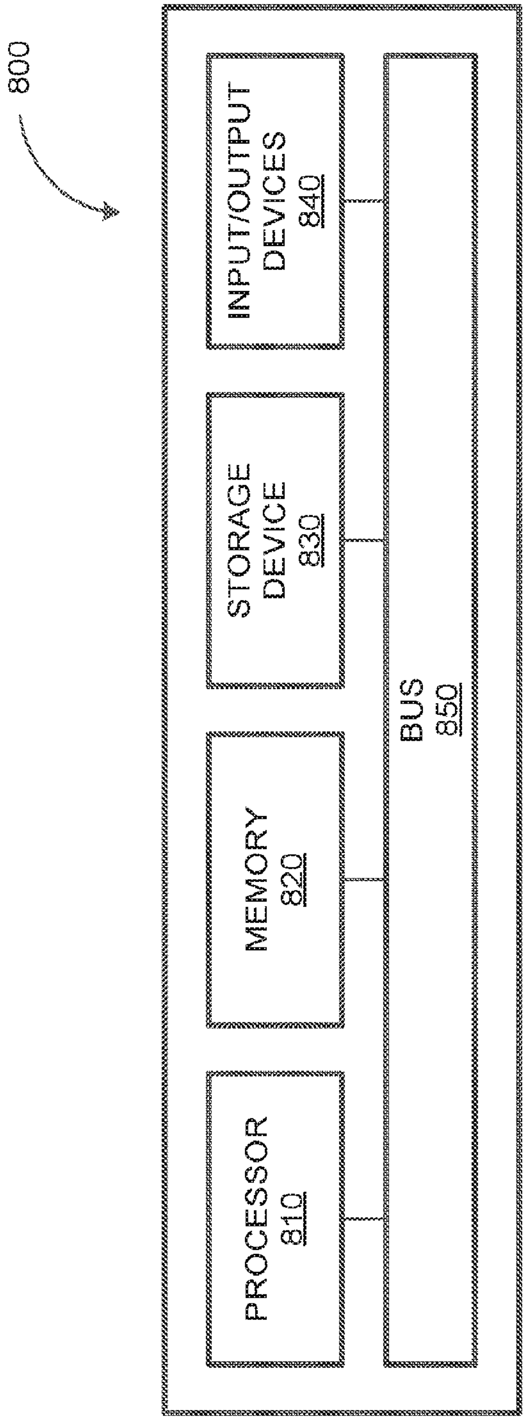
FIG. 8 depicts a block diagram illustrating an example of a computing system, in accordance with some example embodiments.

FIG. 8 depicts a block diagram illustrating an example of a computing system 800, in accordance with some example embodiments. Referring to FIGS. 1-8, the computing system 800 may be used to implement the protein design engine 110, the client device 120, and/or any components therein.

As shown in FIG. 8, the computing system 800 can include a processor 810, a memory 820, a storage device 830, and input/output devices 840. The processor 810, the memory 820, the storage device 830, and the input/output devices 840 can be interconnected via a system bus 850. The processor 810 is capable of processing instructions for execution within the computing system 800. Such executed instructions can implement one or more components of, for example, the protein design engine 110, the client device 120, and/or the like. In some example embodiments, the processor 810 can be a single-threaded processor. Alternately, the processor 810 can be a multi-threaded processor. The processor 810 is capable of processing instructions stored in the memory 820 and/or on the storage device 830 to display graphical information for a user interface provided via the input/output device 840.

The memory 820 is a computer readable medium such as volatile or non-volatile that stores information within the computing system 800. The memory 820 can store data structures representing configuration object databases, for example. The storage device 830 is capable of providing persistent storage for the computing system 800. The storage device 830 can be a floppy disk device, a hard disk device, an optical disk device, or a tape device, or other suitable persistent storage means. The input/output device 840 provides input/output operations for the computing system 800. In some example embodiments, the input/output device 840 includes a keyboard and/or pointing device. In various implementations, the input/output device 840 includes a display unit for displaying graphical user interfaces.

According to some example embodiments, the input/output device 840 can provide input/output operations for a network device. For example, the input/output device 840 can include Ethernet ports or other networking ports to communicate with one or more wired and/or wireless networks (e.g., a local area network (LAN), a wide area network (WAN), the Internet).

In some example embodiments, the computing system 800 can be used to execute various interactive computer software applications that can be used for organization, analysis and/or storage of data in various formats. Alternatively, the computing system 800 can be used to execute any type of software applications. These applications can be used to perform various functionalities, e.g., planning functionalities (e.g., generating, managing, editing of spreadsheet documents, word processing documents, and/or any other objects, etc.), computing functionalities, communications functionalities, etc. The applications can include various add-in functionalities or can be standalone computing products and/or functionalities. Upon activation within the applications, the functionalities can be used to generate the user interface provided via the input/output device 840. The user interface can be generated and presented to a user by the computing system 800 (e.g., on a computer screen monitor, etc.).

One or more aspects or features of the subject matter described herein can be realized in digital electronic circuitry, integrated circuitry, specially designed ASICs, field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including acoustic, speech, or tactile input. Other possible input devices include touch screens or other touch-sensitive devices such as single or multi-point resistive or capacitive track pads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A system, comprising:

at least one data processor; and at least one memory storing instructions which, when executed by the at least one data processor, configures the system to perform operations comprising:

identifying an input sequence;

determining, within the input sequence, an adjustable segment and a fixed segment, wherein the fixed segment is associated with one or more properties of interest;

modifying the input sequence by at least applying a protein design computation model trained to approximate a distribution of protein sequences exhibiting a first property, wherein the protein design computation model modifies the input sequence by at least:

applying an energy-based model (EBM) to modify the adjustable segment of the input sequence, and applying an energy function to determine a likelihood of the modified input sequence being contained within the distribution of protein sequences exhibiting the first property; and generating, based at least on the modified input sequence, an output sequence upon determining that the likelihood of the modified input sequence being contained within the distribution of protein sequences exhibiting the first property satisfies one or more thresholds.

2. The system of claim 1, wherein the energy function is parameterized by a plurality of parameters comprising the EBM.

3. The system of claim 1, wherein the input sequence is modified based at least on an output of the energy function such that each modification increases the likelihood of the modified input sequence being contained within the distribution of protein sequences exhibiting the first property.

4. The system of claim 1, wherein the generating of the output sequence includes:

applying, to the input sequence, a first modification to generate a first modified input sequence;

applying, to the input sequence, a second modification to generate a second modified input sequence;

applying the energy function to determine, for each of the first modified input sequence and the second modified input sequence, a respective likelihood of the first modified input sequence and the second modified input sequence being contained within the distribution of protein sequences exhibiting the first property; and further modifying, based at least on the respective likelihood of each of the first modified input sequence and the second modified input sequence being contained within the distribution, at least one of the first input modified sequence and the second input modified sequence.

5. The system of claim 1, wherein the distribution of protein sequences exhibiting the first property comprises a probability distribution that includes, for each position within a fixed-length sequence, a probability of each possible amino acid residue occupying that position.

6. The system of claim 1, wherein the protein design computation model has been trained to approximate a distribution of protein sequences exhibiting a second property.

7. The system method of claim 6, wherein the input sequence is modified by at least applying a composition of the energy-based model (EBM) and the additional energy-based model (EBM) representative of a joint distribution of protein sequences exhibiting the first property and the second property.

8. The system method of claim 6, wherein the input sequence is modified based at least on a combination of the energy function of the energy-based model and the different energy function of the additional energy-based model.

9. The system of claim 6, wherein the protein design computation model is trained by at least:

adjusting a plurality of parameters of an additional EBM such that different energy function of the additional EBM parameterized by the plurality of parameters of the additional EBM outputs an energy value corresponding to a different likelihood of a sequence being contained within the distribution of protein sequences exhibiting the second property.

10. The system of claim 9, wherein the modifying of the input sequence further includes:

applying the additional EBM to further modify the input sequence;

applying the energy function of the additional energy-based model to determine a likelihood of the further modified input sequence being contained within the distribution of protein sequences exhibiting the second property;

determining a sum of the likelihood of the further modified input sequence being contained within the distribution of protein sequences exhibiting the first property and the likelihood of the further modified input sequence being contained within the distribution of protein sequences exhibiting the second property; and generating the output sequence upon determining that the sum satisfies one or more thresholds.

11. The system of claim 10, wherein the sum corresponds to a likelihood of the modified input sequence being contained within a distribution of protein sequences exhibiting the first property and the second property.

12. The system of claim 11, wherein the input sequence is modified based on the sum such that each modification increases the likelihood of the modified input sequence being contained within the distribution of protein sequences exhibiting the first property and the second property.

13. The system of claim 10, wherein the modifying of the input sequence further includes:

generating a first modified input sequence having a first modification to the input sequence;

determining, based at least on a combination of the energy function of the EBM and the energy function of the additional EBM, an energy value indicative of a likelihood of the first modified input sequence being contained within a distribution of protein sequences exhibiting the first property and the second property;

generating a second modified input sequence having a second modification to the input sequence;

determining, based at least on the combination of the energy function of the EBM and the energy function of the additional EBM, an energy value indicative of a likelihood of the second modified input sequence being contained within the distribution of protein sequences exhibiting the first property and the second property; and further modifying, based at least on the energy value of the first modified input sequence and the energy value of the second modified input sequence, at least one of the first modified input sequence and the second modified input sequence.

14. The system of claim 13, wherein the first modified input sequence is further modified instead of the second modified input sequence based at least on the energy value of the first modified input sequence being lower than the energy value of the second modified input sequence.

15. The system of claim 6, wherein the first property and the second property each comprises a different one of expression, binding affinity towards another molecule, non-specificity, stability, immunogenicity, human-ness, and self-association.

16. The system of claim 6, wherein the protein design computation model has been trained to approximate a distribution of protein sequences exhibiting a third property.

17. The system of claim 1, wherein the operations further comprise:
generating a fixed-length representation of the input sequence, wherein the fixed-length representation of the input sequence includes a gap character at each position in the input sequence without an amino acid residue having a structural role associated with the position; and
applying the EBM to modify the fixed-length representation of the input sequence, wherein the modifying the input sequence includes at least one of
changing one or more identities of one or more amino acid residues at one or more positions within the fixed-length representation of the input sequence,
deleting an amino acid residue occupying a position within the fixed-length representation of the input sequence by at least replacing the amino acid residue with a gap character, and
inserting an amino acid residue at a position within the fixed-length representation of the input sequence by at least replacing a gap residue occupying the position with the amino acid residue.

18. The system of claim 1, wherein the operations further comprise:
identifying a plurality of sample sequences exhibiting the first property; and
training of the protein design computation model by at least adjusting one or more parameters of the energy-based model to increase a similarity between one or more sequences output by the EBM and the plurality of sample sequences.

19. The system of claim 18, wherein the plurality of sample sequences comprises a subset of known protein sequences that excludes one or more known protein sequences failing to exhibit the first property.

20. The system of claim 18, wherein the training of the protein design computation model includes adjusting the one or more parameters of the EBM to increase the likelihood of a sequence generated by the energy-based model being contained within the distribution of protein sequences exhibiting the first property.

21. The system of claim 18, wherein the training of the protein design computation model includes adjusting the one or more of the plurality of parameters of the EBM such that the energy function parameterized by the one or more parameters outputs a lower energy value for a sequence that is contained within the distribution of protein sequences exhibiting the first property than for a second sequence that is outside of the distribution of protein sequences exhibiting the first property.

22. The system of claim 1, wherein the adjustable segment includes a crystallizable fragment (Fc) of an antibody having the input sequence, and wherein the fixed segment includes an antigen binding fragment (Fab), a variable fragment (Fv), a complementarity determining region (CDR), and/or a Vernier zone of the antibody.

23. The system of claim 1, wherein the adjustable segment is associated with one or more undesirable properties.

24. A system, comprising:
at least one data processor; and
at least one memory storing instructions which, when executed by the at least one data processor, configures the system to perform operations comprising:
identifying a plurality of sample sequences exhibiting a first property;
training, based at least on the plurality of sample sequences exhibiting the first property, a protein design computation model to approximate a distribution of protein sequences exhibiting the first property, the training of the protein design computation model includes
adjusting a plurality of parameters of an energy-based model (EBM) to increase a similarity between one or more output sequences of the energy-based model (EBM) and the plurality of sample sequences exhibiting the first property, and
determining an energy function parameterized by the plurality of parameters of the energy-based model to output an energy value corresponding to a likelihood of the one or more output sequences of the energy-based model (EBM) within the distribution of protein sequences exhibiting the first property; and
generating an output sequence exhibiting the first property by at least
determining, within an input sequence, an adjustable segment and a fixed segment, wherein the fixed segment is associated with one or more properties of interest, and
applying the energy-based model (EBM) of the trained protein design computation model to modify, based at least on the energy function of the energy-based model (EBM), the adjustable segment in the input sequence.

25. The system-of claim 24, wherein the operations further comprise:
identifying an additional plurality of sample sequences exhibiting a second property;
further training, based at least on the plurality of sample sequences exhibiting the second property, the protein design computation model to approximate a separate distribution of protein sequences exhibiting the second property, the further training of the protein design computation model includes
adjusting an additional plurality of parameters of an additional energy-based model (EBM) to increase a similarity between one or more output sequences of the additional energy-based model (EBM) and the additional plurality of sample sequences exhibiting the second property, and
determining different energy function parameterized by the plurality of parameters of the additional energy-based model (EBM) to output a separate energy value corresponding to a different likelihood of the one or more output sequences of the additional energy-based mode (EBM) within the distribution of protein sequences exhibiting the second property.

26. The system of claim 25, wherein the generating of the output sequence includes:

applying the energy-based model (EBM) and the additional energy-based model (EBM) to modify the input sequence;

applying the energy function of the energy-based model (EBM) to determine, for the modified input sequence, the energy value indicative of the likelihood of the modified input sequence within the distribution of protein sequences exhibiting the first property;

applying the energy function of the additional energy-based model (EBM) to determine, for the modified input sequence, the separate energy value indicative of the likelihood of the modified input sequence within the separate distribution of protein sequences exhibiting the second property;

determining a sum of the energy value determined by the energy function of the energy-based model (EBM) and the separate energy value determined by the different energy function of the additional energy-based model (EBM);

generating, upon determining that the sum satisfies one or more thresholds, an output sequence based at least on the modified input sequence.

27. The system of claim 24, wherein the training of the protein design computation model includes:

applying the energy-based model (EBM) having one or more adjustments to generate a first plurality of modified sequences;

applying the energy-based model (EBM) having one or more additional adjustments to generate a second plurality of modified sequences;

determining that the first plurality of modified sequences are more similar to the plurality of sample sequences exhibiting the first property than the second plurality of modified sequences; and in response to determining that the first plurality of modified sequences are more similar to the plurality of sample sequences exhibiting the first property than the second plurality of modified sequences, further training the protein design computation model.

28. The system of claim 27, wherein each adjustment includes a change to one or more weights and/or biases of the energy-based model (EBM).

29. The system of claim 24, wherein the energy-based model modifies the input sequence based on an output of the energy function such that each modification increases the likelihood of the modified input sequence being within the distribution of protein sequences exhibiting the first property.

30. A computer-implemented method, comprising:

identifying an input sequence;

determining, within the input sequence, an adjustable segment and a fixed segment, wherein the fixed segment is associated with one or more properties of interest;

modifying the input sequence by at least applying a protein design computation model trained to approximate a distribution of protein sequences exhibiting the first property, wherein the protein design computation model modifies the input sequence by at least:

applying an energy-based model (EBM) to modify the adjustable segment of the input sequence, and applying an energy function to determine a likelihood of the modified input sequence being contained within the distribution of protein sequences exhibiting the first property; and generating, based at least on the modified input sequence, an output sequence upon determining that the likelihood of the modified input sequence being contained within the distribution of protein sequences exhibiting the first property satisfies one or more thresholds.

31. A computer-implemented method, comprising:

identifying a plurality of sample sequences exhibiting a property of interest;

training, based at least on the plurality of sample sequences exhibiting the property of interest, a protein design computation model to approximate a distribution of protein sequences exhibiting the property of interest, the training of the protein design computation model includes adjusting a plurality of parameters of an energy-based model (EBM) to increase a similarity between one or more output sequences of the energy-based model (EBM) and the plurality of sample sequences exhibiting the property of interest, and determining an energy function parameterized by the plurality of parameters of the energy-based model to output an energy value corresponding to a likelihood of the one or more output sequences of the energy-based model (EBM) within the distribution of protein sequences exhibiting the property of interest; and generating an output sequence exhibiting the property of interest by at least applying the energy-based model (EBM) of the trained protein design computation model to modify, based at least on the energy function of the energy-based model (EBM), an input sequence.

* * * * *